(12) United States Patent
Kanamori et al.

(10) Patent No.: US 10,088,409 B2
(45) Date of Patent: Oct. 2, 2018

(54) IMAGE FORMING DEVICE

(71) Applicant: Panasonic Intellectual Property Management Co., Ltd., Osaka (JP)

(72) Inventors: Katsuhiro Kanamori, Nara (JP); Jun Ozawa, Nara (JP)

(73) Assignee: PANASONIC INTELLECTUAL PROPERTY MANAGEMENT CO., LTD., Osaka (JP)

( * ) Notice: Subject to any disclaimer, the term of this patent is extended or adjusted under 35 U.S.C. 154(b) by 0 days.

(21) Appl. No.: 15/792,804

(22) Filed: Oct. 25, 2017

(65) Prior Publication Data

US 2018/0128736 A1    May 10, 2018

(30) Foreign Application Priority Data

Nov. 4, 2016  (JP) ................................ 2016-215898

(51) Int. Cl.
*G01J 4/00*      (2006.01)
*G01N 21/21*   (2006.01)
(Continued)

(52) U.S. Cl.
CPC ............. *G01N 21/21* (2013.01); *A61B 3/14* (2013.01); *G01N 21/8806* (2013.01);
(Continued)

(58) Field of Classification Search
CPC ............. G01N 21/211; G01N 21/21; G01N 2021/213; G01J 4/00; G01B 11/0641
(Continued)

(56) References Cited

U.S. PATENT DOCUMENTS 5,738,429 A * 4/1998 Tagawa ................ G03B 21/132
                                                              353/122
9,645,074 B2 * 5/2017 Kanamori .............. G01N 21/21
(Continued)

FOREIGN PATENT DOCUMENTS

JP     2008-053787     3/2008
JP     2011-150689     8/2011
(Continued)

OTHER PUBLICATIONS

Neil T. Clancy et al., "Polarised stereo endoscope and narrowband detection for minimal access surgery", Biomedical Optics Express 5(12), Nov. 2014, 4108-4117.
(Continued)

*Primary Examiner* — Md M Rahman
(74) *Attorney, Agent, or Firm* — Wenderoth, Lind & Ponack, L.L.P.

(57) ABSTRACT

Images are formed from first and second polarized images acquired through illumination of the subject with first illumination light beams, and third and fourth polarized images acquired through illumination of the subject with second illumination light beams. Images of a subject are formed from translated first, second, third, and fourth polarized images, acquired from first and second luminous point images. The first bright spots appear on the first polarized image when the first illumination light beams are mirror-reflected off the subject. The second bright spots appear on the fourth polarized image when the second illumination light beams are mirror-reflected off the subject. The image forming circuit forms images of the subject by calculating a difference between a first average image, obtained by averaging the translated first and fourth polarized images, and a second average image, obtained by averaging the translated second and third polarized images.

7 Claims, 17 Drawing Sheets

(51) Int. Cl.
 *G02B 27/28* (2006.01)
 *G01N 21/88* (2006.01)
 *A61B 3/14* (2006.01)
 *G01N 21/958* (2006.01)
(52) U.S. Cl.
 CPC ........... *G01N 21/958* (2013.01); *G02B 27/28* (2013.01); *G01N 2021/8848* (2013.01); *G06T 2207/20216* (2013.01)
(58) Field of Classification Search
 USPC ........................................................ 356/369
 See application file for complete search history.

(56) References Cited

U.S. PATENT DOCUMENTS

| | | |
|---|---|---|
| 2012/0242835 A1 | 9/2012 | Li et al. |
| 2015/0219552 A1 | 8/2015 | Kanamori |
| 2015/0234150 A1 | 8/2015 | Katsunuma et al. |

FOREIGN PATENT DOCUMENTS

| | | |
|---|---|---|
| JP | 2011-205215 | 10/2011 |
| JP | 2012-165207 | 8/2012 |
| JP | 2013-036908 | 2/2013 |
| JP | 2015-164518 | 9/2015 |
| JP | 2016-105044 | 6/2016 |
| WO | 2013/179620 | 12/2013 |

OTHER PUBLICATIONS

Katsuhiro Kanamori, "Image enhancement of surface microstructure on mucosa for polarimetric endoscopy", Proc. of SPIE vol. 9318, Mar. 2015, 93180O-1 to 93180O-14.

* cited by examiner

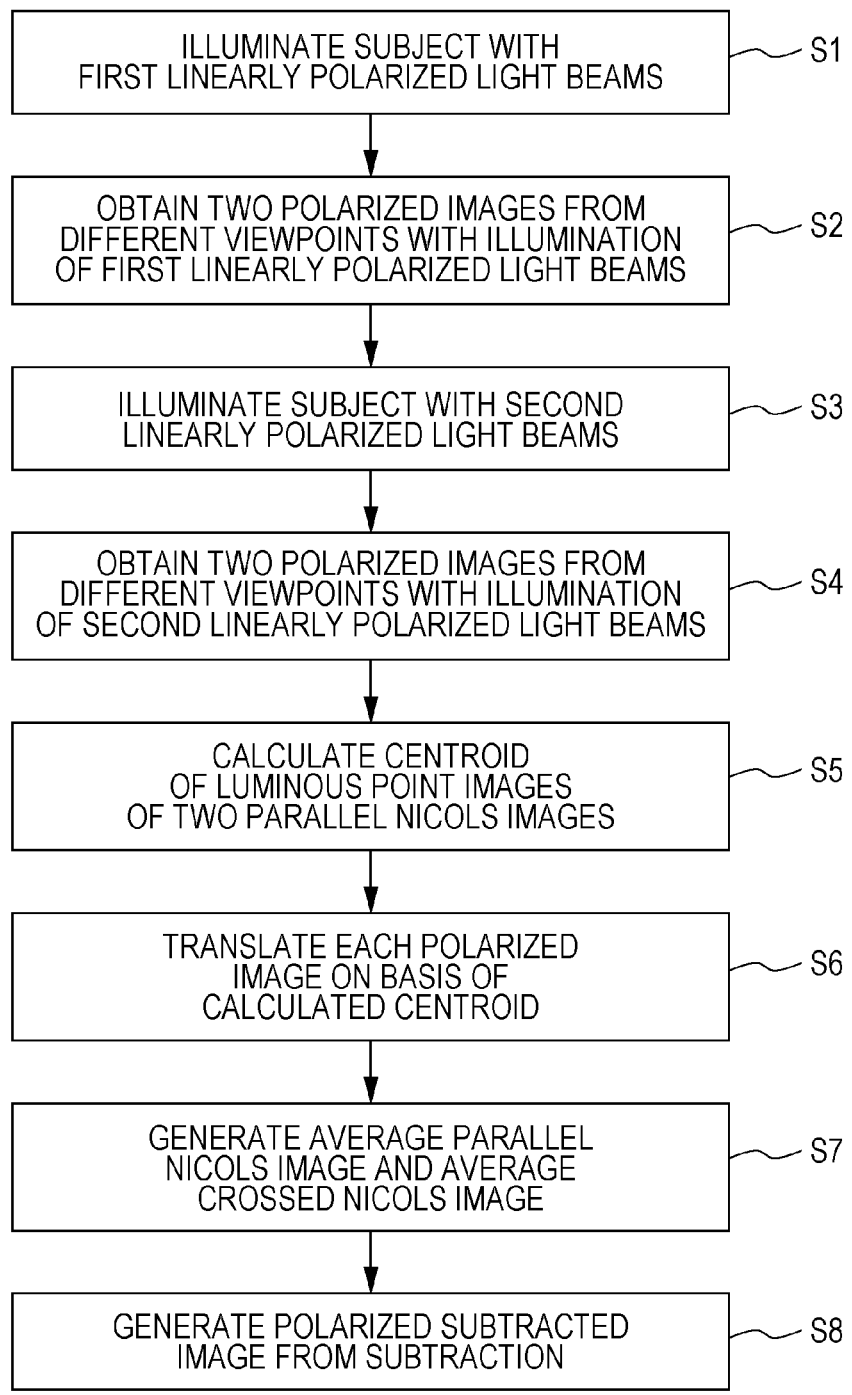

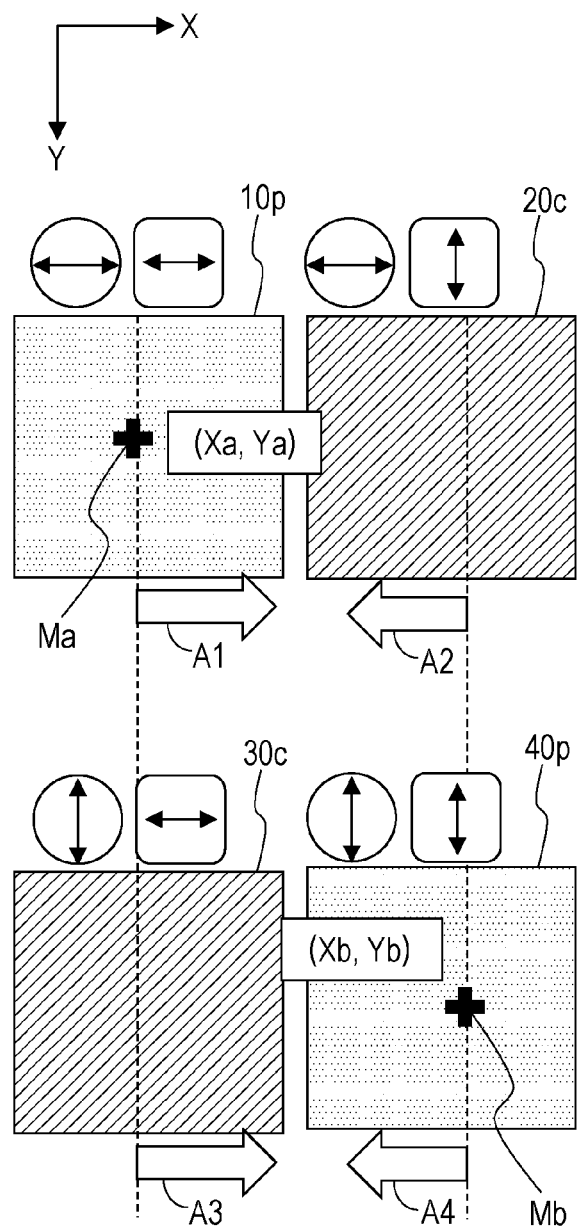

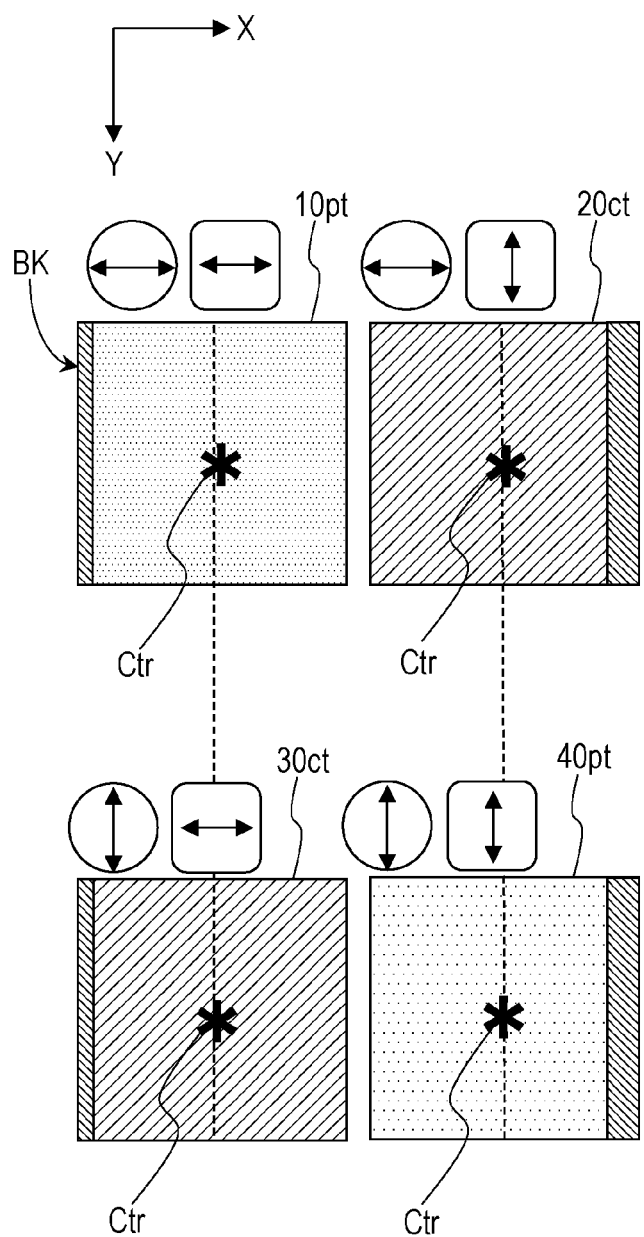

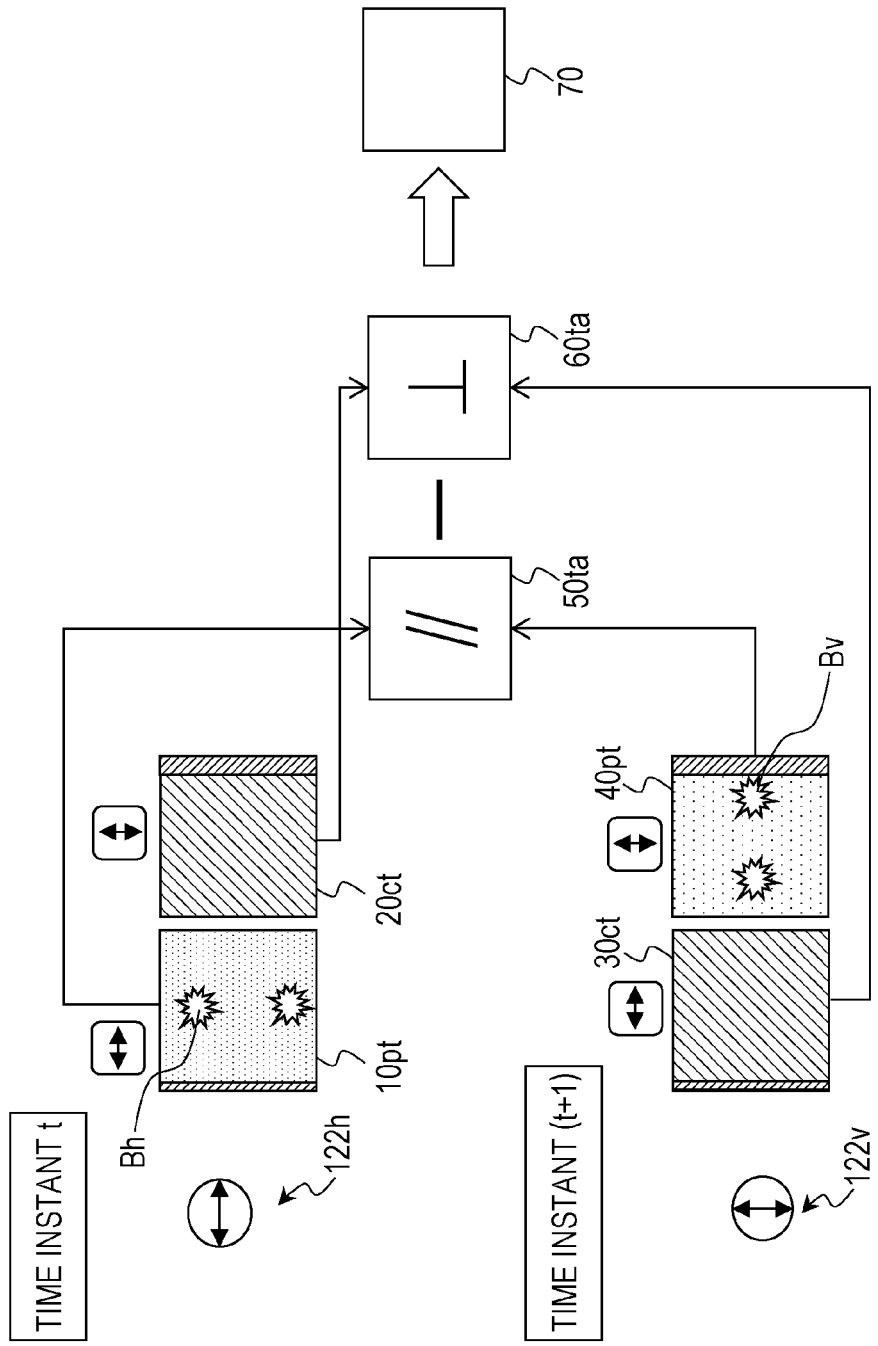

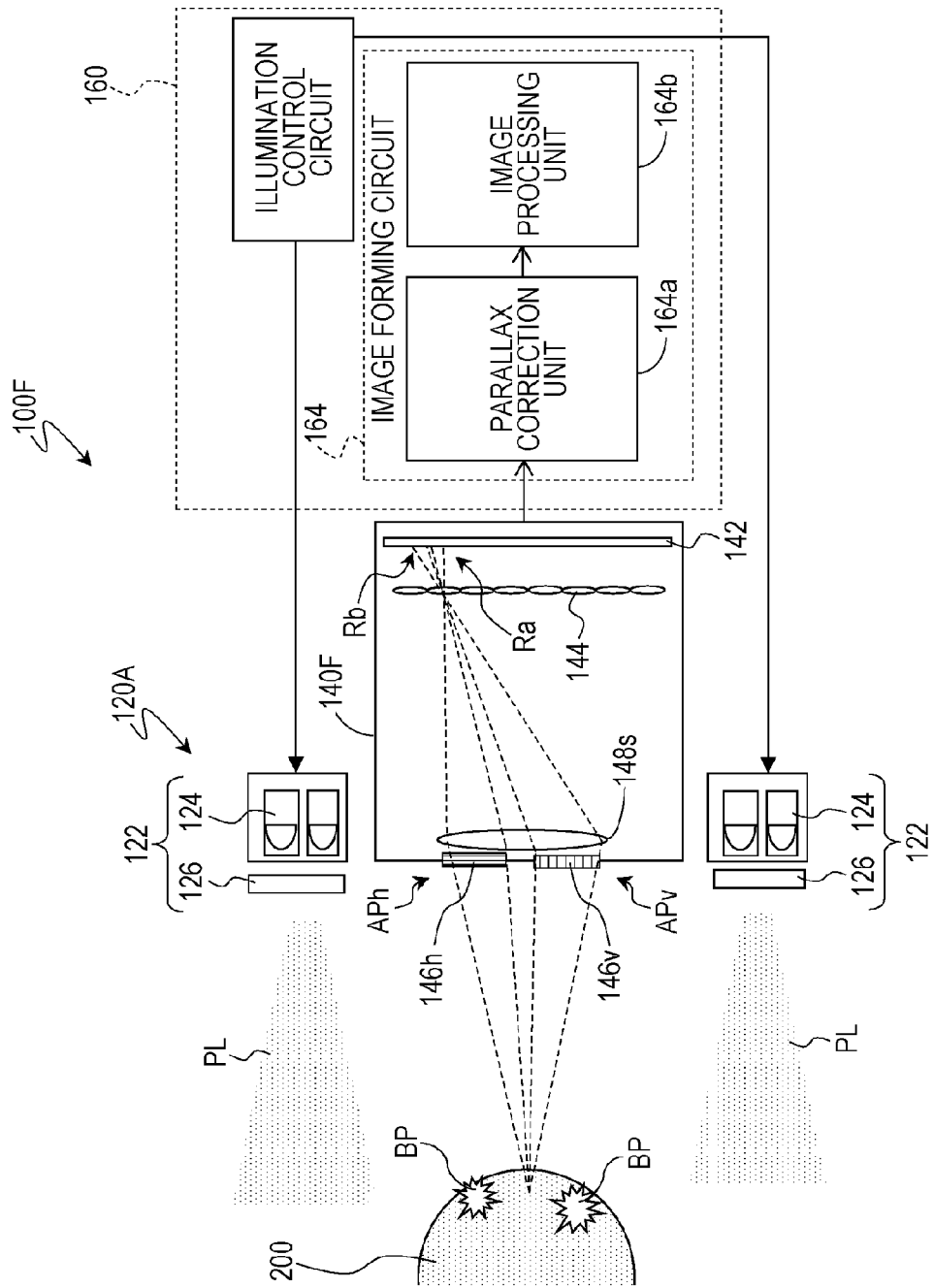

IMAGE FORMING DEVICE

BACKGROUND

1. Technical Field

The present disclosure relates to an image forming device.

2. Description of the Related Art

Polarization imaging is known to be effective in detecting a foreign substance adhering to a transparent object and the state of the surface of a transparent object. For example, Japanese Unexamined Patent Application Publication No. 2013-036908 discloses a surface observing device, which sequentially illuminates a transparent plate member with linearly polarized light beams perpendicular to each other, obtains first and second polarized images through illumination with the corresponding linearly polarized light beams, and detects a foreign substance using a composite image of the first and second polarized images.

Japanese Unexamined Patent Application Publication No. 2015-164518 and Katsuhiro Kanamori, "Image enhancement of surface micro-structure on mucosa for polarimetric endoscopy", Proceedings of SPIE, 2015, Vol. 9318, 93180O-1 to 93180O-14 disclose a use of polarization imaging to observe a fine structure of a tissue surface covered with a semitransparent mucous membrane. The technologies described in Japanese Unexamined Patent Application Publication No. 2015-164518 and Katsuhiro Kanamori, "Image enhancement of surface micro-structure on mucosa for polarimetric endoscopy", Proceedings of SPIE, 2015, Vol. 9318, 93180O-1 to 93180O-14 include acquisition of parallel nicols images and crossed nicols images from linearly polarized light beams, serving as illumination light beams, whose planes of polarization differ by 90° from each other, averaging two parallel nicols images and two crossed nicols images to acquire average images, and subjecting the average image of the two parallel nicols images and the average image of the two crossed nicols images to subtraction. According to Japanese Unexamined Patent Application Publication No. 2015-164518 and Katsuhiro Kanamori, "Image enhancement of surface micro-structure on mucosa for polarimetric endoscopy", Proceedings of SPIE, 2015, Vol. 9318, 93180O-1 to 93180O-14, such processing enables acquisition of an image of a subject surface having fine projections and depressions enhanced. Neil T. Clancy, Shobhit Arya, Ji Qi, Danail Stoyanov, George B. Hanna, and Daniel S. Elson, "Polarised stereo endoscope and narrowband detection for minimal access surgery", Biomedical Optics Express, 1 Dec. 2014, Vol. 5, No. 12, pp 4108-4117 disclose a multi-lens rigid endoscope including a linearly-polarized-light illuminating unit and two polarizers having transmission axes oriented in different directions, which are located at the distal end, and two charge-coupled devices (CCDs) corresponding to the two polarizers. The entire contents of Japanese Unexamined Patent Application Publication No. 2015-164518 and Katsuhiro Kanamori, "Image enhancement of surface micro-structure on mucosa for polarimetric endoscopy", Proceedings of SPIE, 2015, Vol. 9318, 93180O-1 to 93180O-14 are incorporated herein by reference.

The surface observing device disclosed in Japanese Unexamined Patent Application Publication No. 2013-036908 includes microlenses and a polarizing filter having a polarization pattern in front of an image sensor. Such a structure requires a high technology to form a fine polarization pattern and precise positioning of the microlenses and the polarization pattern so that they correspond to a light-receptive area of the image sensor. On the other hand, a multi-lens polarizing camera disclosed by Neil T. Clancy, Shobhit Arya, Ji Qi, Danail Stoyanov, George B. Hanna, and Daniel S. Elson, "Polarised stereo endoscope and narrowband detection for minimal access surgery", Biomedical Optics Express, 1 Dec. 2014, Vol. 5, No. 12, pp 4108-4117, does not basically require positioning between the light-receptive areas of the image sensor and the polarization pattern, and thus can have a more flexible design. Such a multi-lens polarizing camera is also advantageous from the viewpoint of an increase of an exposure value.

The multi-lens structure, however, essentially involves parallax. Neil T. Clancy, Shobhit Arya, Ji Qi, Danail Stoyanov, George B. Hanna, and Daniel S. Elson, "Polarised stereo endoscope and narrowband detection for minimal access surgery", Biomedical Optics Express, 1 Dec. 2014, Vol. 5, No. 12, pp 4108-4117, describe that a pixel value of each pixel is calculated to cancel parallax by detecting projections in multiple images captured by cameras and aligning the projections between the images. The technology disclosed by Neil T. Clancy, Shobhit Arya, Ji Qi, Danail Stoyanov, George B. Hanna, and Daniel S. Elson, "Polarised stereo endoscope and narrowband detection for minimal access surgery", Biomedical Optics Express, 1 Dec. 2014, Vol. 5, No. 12, pp 4108-4117 is considered to be effective when the subject has texture. On the other hand, a subject having a smooth surface does not allow the projections to be associated with each other between the images.

SUMMARY

In one general aspect, the techniques disclosed here feature an image forming device that includes a plurality of first light emitting units that illuminate a subject with first illumination light beams polarized in a first direction, a plurality of second light emitting units that illuminate the subject with second illumination light beams polarized in a second direction crossing the first direction, an imaging device having an imaging surface including a first area, which receives first reflection light beams polarized in the first direction, and a second area, which receives second reflection light beams polarized in the second direction, and an image forming circuit that forms an image of the subject on the basis of a first polarized image relating to the first reflection light beams, a second polarized image relating to the second reflection light beams, a third polarized image relating to the first reflection light beams, and a fourth polarized image relating to the second reflection light beams, the first polarized image and the second polarized image being captured by the imaging device while the subject is illuminated with the first illumination light beams, and the third polarized image and the fourth polarized image being captured by the imaging device while the subject is illuminated with the second illumination light beams. The centroid of a geometric shape connecting positions of the plurality of first light emitting units coincides with the centroid of a geometric shape connecting positions of the plurality of second light emitting units. The image forming circuit forms an image of the subject from a translated first polarized image, a translated second polarized image, a translated third polarized image, and a translated fourth polarized image, which are obtained from images of a plurality of first bright spots and images of a plurality of second bright spots, the first bright spots appearing on the first polarized image when the first illumination light beams are mirror-reflected off the subject, and the second bright spots appearing on the fourth polarized image when the second illumination light beams are mirror-reflected off the subject. The image forming circuit forms an image of the subject by calculating a difference between a first average image and a second average image, the first average image being obtained by averaging the translated first polarized image and the translated fourth polarized image, the second average image being obtained by averaging the translated second polarized image and the translated third polarized image.

These general and specific aspects may be implemented using a system, a method, an integrated circuit, a computer program, and a computer-readable recording medium, and any combination of a device, a system, a method, an integrated circuit, a computer program, and a computer-readable recording medium. Examples of a computer-readable recording medium include a nonvolatile recording medium such as a compact disc read-only memory (CD-ROM).

The present disclosure enables polarization imaging that prevents the effect of parallax. Additional benefits and advantages of the disclosed embodiments will become apparent from the specification and drawings. The benefits and/or advantages may be individually obtained by the various embodiments and features of the specification and drawings, which need not all be provided in order to obtain one or more of such benefits and/or advantages.

BRIEF DESCRIPTION OF THE DRAWINGS

FIG. 3 is a schematic diagram of a typical process performed by an illumination control circuit and an image forming circuit;

FIG. 5A is a schematic diagram illustrating an example of parallax correction performed by a parallax correction unit in the state before parallax correction;

FIG. 5B is a schematic diagram illustrating an example of parallax correction performed by the parallax correction unit in the state after parallax correction;

FIG. 6 is a schematic diagram of a typical process performed by an image processing unit;

FIG. 16 is a diagram of an example of an imaging device having a different structure used together with the illuminating device;

DETAILED DESCRIPTION

Figure 1:
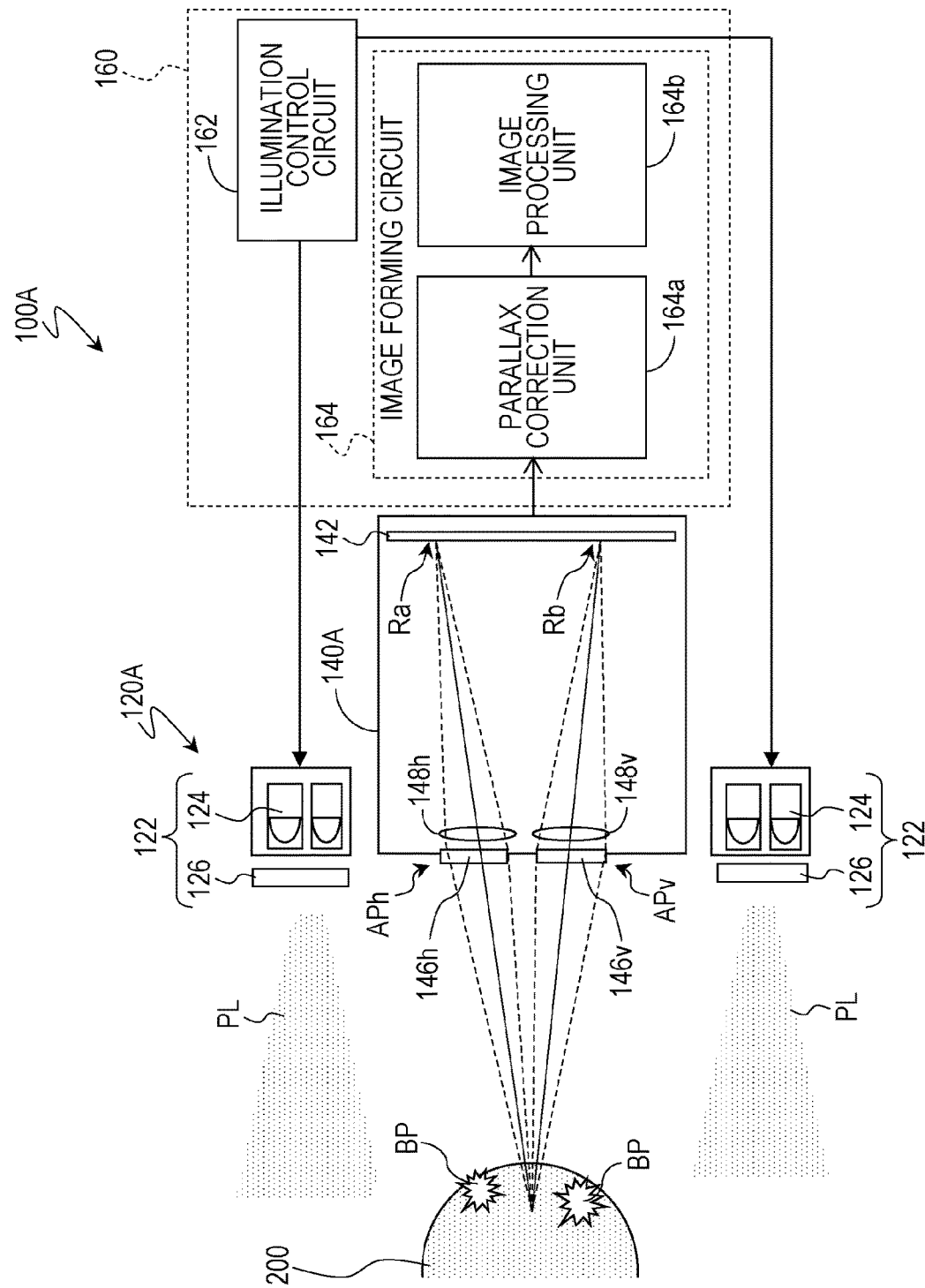
FIG. 1 is a diagram illustrating, by way of example, a structure of an image forming device according to a first embodiment of the disclosure.

Aspects of the present disclosure are schematically described as follows.

First Aspect

An image forming device includes a plurality of first light emitting units that illuminate a subject with first illumination light beams polarized in a first direction, a plurality of second light emitting units that illuminate the subject with second illumination light beams polarized in a second direction crossing the first direction, an imaging device having an imaging surface including a first area, which receives first reflection light beams polarized in the first direction, and a second area, which receives second reflection light beams polarized in the second direction, and an image forming circuit that forms an image of the subject on the basis of a first polarized image relating to the first reflection light beams, a second polarized image relating to the second reflection light beams, a third polarized image relating to the first reflection light beams, and a fourth polarized image relating to the second reflection light beams, the first polarized image and the second polarized image being captured by the imaging device while the subject is illuminated with the first illumination light beams, and the third polarized image and the fourth polarized image being captured by the imaging device while the subject is illuminated with the second illumination light beams. The centroid of a geometric shape connecting positions of the plurality of first light emitting units coincides with the centroid of a geometric shape connecting positions of the plurality of second light emitting units. The image forming circuit forms an image of the subject from a translated first polarized image, a translated second polarized image, a translated third polarized image, and a translated fourth polarized image, which are obtained from images of a plurality of first bright spots and images of a plurality of second bright spots. The first bright spots appear on the first polarized image when the first illumination light beams are mirror-reflected off the subject. The second bright spots appear on the fourth polarized image when the second illumination light beams are mirror-reflected off the subject. The image forming circuit forms an image of the subject by calculating a difference between a first average image and a second average image, the first average image being obtained by averaging the translated first polarized image and the translated fourth polarized image, the second average image being obtained by averaging the translated second polarized image and the translated third polarized image.

Second Aspect

In the image forming device according to the first aspect, the plurality of first light emitting units and the plurality of second light emitting units are arranged in a circle, and the center of a circle that passes the positions of the plurality of first light emitting units coincides with the center of a circle that passes the positions of the plurality of second light emitting units.

Third Aspect

In the image forming device according to the first or second aspect, the plurality of first light emitting units and the plurality of second light emitting units surround the imaging device when viewed from the subject.

Fourth Aspect

The image forming device according to any one of the first to third aspects further includes an illumination control circuit. In the image forming device, the plurality of first light emitting units each include a first light source, the plurality of second light emitting units each include a second light source, and the illumination control circuit lights the first light source and the second light source at a different time point.

Fifth Aspect

In the image forming device according to any one of the first to fourth aspects, the image forming circuit translates the first polarized image so that the centroid of the images of the plurality of first bright spots in the first polarized image is located at the center of the first polarized image, and translates the third polarized image in a direction the same as a direction in which and by a distance the same as a distance by which the first polarized image is translated. The image forming circuit translates the fourth polarized image so that the centroid of the images of the plurality of second bright spots in the fourth polarized image is located at the center of the fourth polarized image, and translates the second polarized image in a direction the same as a direction in which and by a distance the same as a distance by which the fourth polarized image is translated.

Sixth Aspect

The image forming device according to any one of the first to fifth aspects, further includes at least one first image sensor device including a first area, and at least one second image sensor device including a second area.

Embodiments of the present disclosure will now be described in detail with reference to the drawings. Embodiments described below are general or specific examples. The numerical values, shapes, materials, components, arrangement of the components, connection between the components, steps, order of steps, and other parameters described in the embodiments are mere examples and not intended to limit the present disclosure. Various aspects described herein can be combined together unless they are incompatible with each other. Among components of the embodiments described below, components not included in the independent claim representing the most superordinate concept are described as optional components. In the following description, components having substantially the same functions are denoted with the same reference signs and may not be described.

First Embodiment

FIG. 1 is a diagram illustrating, by way of example, a structure of an image forming device according to a first embodiment of the disclosure. An image forming device 100A illustrated in FIG. 1 schematically includes an illuminating device 120A, including multiple light emitting units 122, an imaging device 140A, and a control circuit 160. The illuminating device 120A illuminates a subject 200 with linearly polarized light beams. The imaging device 140A captures an image of the subject 200 illuminated with the linearly polarized light beams.

Each of the multiple light emitting units 122 includes light sources 124 and a polarizer 126 positioned in front of the light source 124. Examples usable as the light sources 124 include known light-emitting devices such as a white light-emitting diode and an infrared-emitting diode. Examples usable as the polarizer 126 include a commercially available polarizing sheet and a metal wire grid polarizer.

The multiple light emitting units 122 include at least two types of polarizers whose transmission axes are oriented in different directions. Thus, each light emitting unit 122 emits linearly polarized light beams PL in the direction of the transmission axis of the polarizer 126. As described below, under the control of the control circuit 160, the illuminating device 120A selectively lights at least two of the multiple light sources 124, in front of which the polarizers 126 having the transmission axes oriented in the same direction are disposed, to sequentially illuminate the subject 200 with light beams having different planes of polarization.

Typically, the subject 200 is a transparent or semitransparent object having a smooth surface. Examples of the subject 200 include a human or animal eyeball and a transparent pill package. As schematically illustrated in FIG. 1, when the subject 200 is illuminated with linearly polarized light beams PL from multiple positions, multiple bright spots BP attributable to mirror reflection appear on the subject 200. The positions of these bright spots BP reflect the positions of the light sources 124 lit during image capturing.

The imaging device 140A includes an image sensor device 142 and an optical system that forms an image of the subject 200 on the imaging surface of the image sensor device 142. Examples usable as the image sensor device 142 include a CCD image sensor, a complementary MOS (CMOS) image sensor, and a multi-layer image sensor including an organic or inorganic photoelectric conversion layer on top of a semiconductor substrate. Specifically, the image sensor device 142 includes multiple pixels. The imaging device 140A with the structure illustrated in FIG. 1 by way of example includes analyzers 146h and 146v arranged corresponding to two apertures APh and APv in the housing of the imaging device 140A. The analyzers 146h and 146v selectively transmit therethrough linearly polarized light beams having transmission axes oriented in different directions and having different planes of polarization. In the same manner as the polarizer 126 of each light emitting unit 122, examples usable as the analyzers 146h and 146v include a commercially available polarizing sheet and a metal wire grid polarizer.

In this example, an objective lens 148h is interposed between the analyzer 146h and the image sensor device 142, and an objective lens 148v is interposed between the analyzer 146v and the image sensor device 142. Of reflection light beams from the subject 200, a light beam that has passed through the analyzer 146h passes through the objective lens 148h and forms an image on the imaging surface of the image sensor device 142. Similarly, of reflection light beams from the subject 200, a light beam that has passed through the analyzer 146v passes through the objective lens 148v and forms an image on the imaging surface of the image sensor device 142. Here, of light beams from the same point on the subject 200, one that has passed through the analyzer 146h and another one that has passed through the analyzer 146v form images at different points on the imaging surface. In other words, the imaging surface of the image sensor device 142 includes an area Ra on which light beams that have passed through the analyzer 146h are incident and an area Rb on which light beams that have passed through the analyzer 146v are incident. When signals of the light beams incident on the area Ra and signals of the light beams incident on the area Rb are individually acquired from the image sensor device 142, images viewed from the position of the objective lens 148h and images viewed from the position of the objective lens 148v can be formed.

Here, the analyzers 146h and 146v have transmission axes oriented in different directions. Each of the areas Ra and Rb can thus be said as being an area receiving, of light beams returned from the subject 200, light beams polarized in a specific direction (for example, horizontal direction) or light beams polarized in another direction (for example, vertical direction). A signal of a light beam incident on the area Ra represents an image based on, of light beams returned from the subject 200, a specific light beam polarized in a specific direction (for example, horizontal direction). A signal of a light beam incident on the area Rb represents an image based on, of light beams returned from the subject 200, a specific light beam polarized in another direction (for example, vertical direction). In this manner, the imaging device 140A can collectively acquire signals of images based on light breams polarized in a specific state and signals of images based on light beams polarized in another specific state. These signals of the images are signals of images viewed from the positions of the apertures APh and APv and these images thus have parallax between each other. For convenience's sake, images of light beams polarized in a specific state may be referred to as "polarized images".

As described below, a typical embodiment of the disclosure captures an image while at least two of the multiple light sources 124 included in the illuminating device 120A, in front of which the polarizers 126 having the transmission axes oriented in the same direction are disposed, are selectively lit in sequence. Thus, a typical embodiment of the disclosure can acquire multiple pairs of polarized images from different viewpoints and corresponding to the polarized states of light beams with which the subject 200 is illuminated. A typical embodiment of the present disclosure forms an image of a subject on the basis of multiple polarized images acquired from illumination light beams polarized in different states. As described above, a polarized image is acquired by image capturing while at least two of the multiple light sources 124, in front of which the polarizers 126 having the transmission axes oriented in the same direction are disposed, are selectively lit. At this time, as schematically illustrated in FIG. 1, images of light beams from the light sources 124 lit during image capturing appear on the subject 200 in the form of bright spotbright spots BP. Thus, images of the bright spot bright spots BP on the subject 200 appear in the acquired polarized images. Multiple pixel values at multiple pixel positions at which the images of the bright spotbright spots BP appear are greater than the multiple pixel values at multiple pixel positions at which the images of the bright spot bright spots BP do not appear. The position of the image of each bright spot t BP reflects the position of the corresponding light source 124 lit during the image capturing. As described below in detail, a typical embodiment of the present disclosure performs parallax correction using the position of the image of a bright spot BP in an acquired image.

In the structure illustrated in FIG. 1 by way of example, the control circuit 160 includes an illumination control circuit 162, which controls the operation of the illuminating device 120A, and an image forming circuit 164, which forms an image of the subject 200 on the basis of signals from the imaging device 140A. In this example, the image forming circuit 164 includes a parallax correction unit 164a and an image processing unit 164b. The parallax correction unit 164a performs correction by cancelling parallax between polarized images from different viewpoints. The image processing unit 164b forms images of the subject 200 on the basis of multiple polarized images. As described below, in the example described here, the image processing unit 164b generates image data of the subject 200 on the basis of outputs from the parallax correction unit 164a. Typical examples of the operation of the control circuit 160 are described below in details.

The control circuit 160 may be, for example, a microcontroller including a central processing unit (CPU). The illumination control circuit 162, and the parallax correction unit 164a and the image processing unit 164b of the image forming circuit 164 may each be a part of a single microcontroller or may be separate processing circuits. For example, the parallax correction unit 164a and/or the image processing unit 164b may be implemented by, for example, a digital signal processor (DSP), an application specific integrated circuit (ASIC), or a field-programmable gate array (FPGA).

Figure 2:
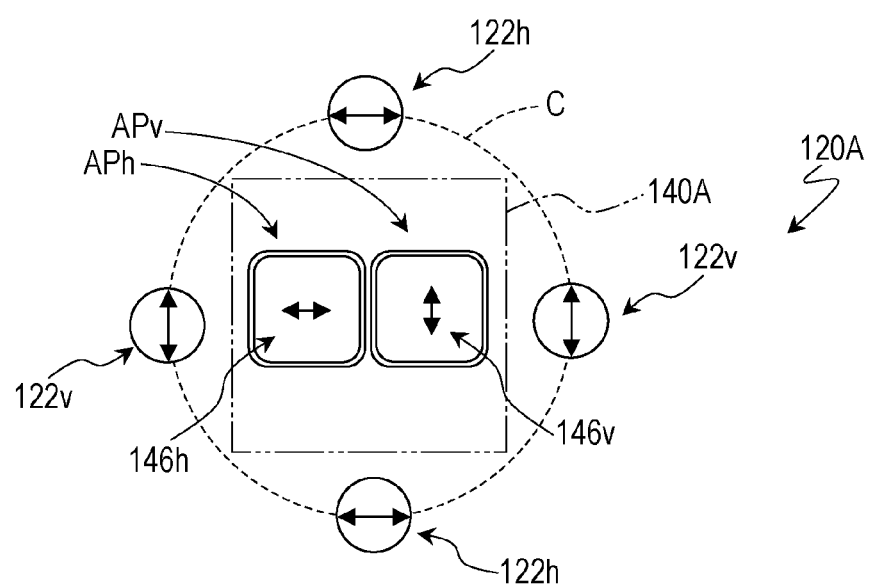
FIG. 2 is a diagram of an example of a typical arrangement of multiple light emitting units and two apertures in an imaging device when viewed from a subject.

FIG. 2 is a diagram of an example of a typical arrangement of the multiple light emitting units 122 and the two apertures APh and APv in the imaging device 140A when viewed from the subject 200. In the example illustrated in FIG. 2, the illuminating device 120A includes a pair of light emitting units 122h and a pair of light emitting units 122v. Typically, the light emitting units 122h and 122v in the illuminating device 120A are arranged on the same plane. FIG. 2 illustrates a typical arrangement of the two light emitting units 122h and the two light emitting units 122c when viewed from the subject 200 in the direction normal to the plane on which the light emitting units 122h and 122v are arranged.

Here, the apertures APh and APv of the imaging device 140A are also located on the same plane on which the two light emitting units 122h and the two light emitting units 122v are arranged. In the structure illustrated in FIG. 2 by way of example, the two light emitting units 122h and the two light emitting units 122v are respectively arranged in the vertical direction and the lateral direction of the drawing, so as to surround the two apertures APh and APv in the imaging device 140A when viewed from the subject 200 in the direction normal to the plane on which the light emitting units 122h and 122v are arranged.

FIG. 2 illustrates, by way of example, a structure in which the intermediate point between the two light emitting units 122h coincides with the intermediate point between the two light emitting units 122v. In other words, the centroid of a geometric shape (here, a line segment) connecting the positions of the two light emitting units 122h coincides with the centroid of a geometric shape (here, a line segment) connecting the positions of the two light emitting units 122v. In the structure illustrated in FIG. 2 by way of example, the light emitting units 122h and 122v can be said as having a ring-shaped arrangement. Particularly, in this example, when viewed from the subject 200, the light emitting units 122h and the light emitting units 122v are alternately arranged at positions 90° rotated apart from each other on the circumference of a virtual circle C drawn with a broken line in FIG. 2. Concurrently, the light emitting units 122h and 122v surround the imaging device 140A. The multiple light emitting units 122 arranged in a ring shape can uniformly illuminate the subject 200.

When multiple first emitting surfaces included in the multiple light emitting units 122h and emitting light beams to the outside of the multiple light emitting units 122h are multiple first circles, multiple first centers of the multiple first circles serve as multiple first centers of the multiple first emitting surfaces. The multiple first emitting surfaces, the multiple first circles, and the multiple first centers correspond one to one.

In the example of FIG. 2, the multiple first emitting surfaces include an upper emitting surface of the light emitting unit located on the upper side in FIG. 2 and a lower emitting surface of the light emitting unit located on the lower side in FIG. 2. The multiple first centers include the center of an upper circular surface, serving as an upper emitting surface, and the center of a lower circular surface, serving as a lower emitting surface.

When multiple second emitting surfaces included in the multiple light emitting units 122v and emitting light beams to the outside of the multiple light emitting units 122v are multiple second circles, multiple second centers of the multiple second circles serve as multiple second centers of the multiple second emitting surfaces. The multiple second emitting surfaces, the multiple second circles, and the multiple second centers correspond one to one.

For example, in the example of FIG. 2, the multiple second emitting surfaces include a left emitting surface of the light emitting unit located on the left side in FIG. 2 and a right emitting surface of the light emitting unit located on the right side in FIG. 2. The multiple second centers include the center of a left circular surface, serving as a left emitting surface, and the center of a right circular surface, serving as a right emitting surface. The geometric centroid of the multiple first centers may coincide with the geometric centroid of the multiple second centers.

In the example of FIG. 2, the geometric centroid for the centers of the upper and lower circular surfaces, serving as the geometric centroid of the multiple first centers, may coincide with the geometric centroid for the centers of the left and right circular surfaces, serving as the geometric centroid of the multiple second centers.

The multiple light emitting units 122 do not necessarily have to surround the imaging device 140A. As is clear from the parallax correction principle, described below, when the light emitting unit 122 includes a pair of light emitting units 122h and a pair of light emitting units 122v, it suffices that they are arranged so that the intermediate point between the two light emitting units 122h coincides with the intermediate point between the two light emitting units 122v. Specifically, the imaging device 140A may be located on the outer side of the circle C defined by these light emitting units. Nevertheless, from the size reduction point of view, the multiple light emitting units 122 arranged so as to surround the imaging device 140A are advantageous. In addition, the multiple light emitting units 122 arranged so as to surround the imaging device 140A enable illumination approximate to coaxial illumination.

In FIG. 2, thick double-sided arrows enclosed in the circles at the positions of the light emitting units 122h and 122v schematically indicate the directions of the transmission axes of the polarizers 126 (see FIG. 1). As illustrated in FIG. 2, in this example, the transmission axes of the polarizers 126 of the light emitting units 122h extend in a direction parallel to the lateral direction in the drawing (for example, horizontal direction). On the other hand, the transmission axes of the polarizers 126 of the light emitting units 122v extend in a direction perpendicular to the direction of the transmission axes of the polarizers 126 of the light emitting units 122h. Here, the direction of the transmission axes of the polarizers 126 of the light emitting units 122v is parallel to the vertical direction in the drawing, and perpendicular to the direction of the transmission axes of the polarizers 126 of the light emitting units 122h. The following describes, by way of example, a structure in which the direction of the transmission axes of the polarizers 126 of the light emitting units 122h is perpendicular to the direction of the transmission axes of the polarizers 126 of the light emitting units 122v. Arranging the polarizers 126 of the light emitting units 122h to have their transmission axes extending in a direction perpendicular to the transmission axes of the polarizers 126 of the light emitting units 122v is not necessary. However, the arrangement in which they are perpendicular to each other is advantageous from the light use efficiency. Also in other drawings of the present disclosure, the directions of the transmission axes of the polarizers 126 may be drawn with thick double-sided arrows enclosed in circles, as illustrated in FIG. 2.

In the structure illustrated in FIG. 2 by way of example, the apertures APh and APv (or referred to as viewpoints) are located substantially the center of the circle C defined by the light emitting units 122h and 122v adjacent to each other in the lateral direction in the drawing. The distance between the centers of the apertures APh and APv can fall within, for example, a range of approximately 1.0 mm to 10 mm. In FIG. 2, the thick double-sided arrows enclosed in rounded rectangles schematically indicate the directions of the transmission axes of the analyzers 146h and 146v (see FIG. 1) arranged in the apertures APh and APv. Also in other drawings of the present disclosure, the directions of the transmission axes of the analyzers may be indicated with thick double-sided arrows enclosed in rounded rectangles, below. Multiple first surfaces that are included in the multiple light emitting units 122h and emit light beams to the outside of the multiple light emitting units 122h may be arranged on a first plane, on which multiple second surfaces that are included in the multiple light emitting units 122v and emit light beams to the outside of the multiple light emitting units 122v are arranged. A third surface that is included in the analyzer 146h and receives light beams from the outside of the analyzers 146h may be arranged on a second plane, on which a fourth surface that is included in the analyzer 146v and receives light beams from the outside of the analyzer 146v is arranged. The first plane and the second plane may be the same plane.

As illustrated in the drawing, the transmission axis of the analyzer 146h extends in a direction parallel to the lateral direction of the drawing, and the transmission axis of the analyzer 146v extends in a direction parallel to the vertical direction of the drawing. Specifically, the direction parallel to the direction of the transmission axes of the polarizers 126 of the light emitting units 122h is selected as the direction of the transmission axis of the analyzer 146h, and the direction parallel to the direction of the transmission axes of the polarizers 126 of the light emitting units 122v is selected as the direction of the transmission axis of the analyzer 146v. Selecting the direction of the transmission axes in this manner enables acquiring of the following polarized images. Specifically, polarized images based on the light beams that have a plane of polarization the same as that of the linearly polarized light beams emitted from the light emitting units 122h can be acquired from the light beams returned from the subject 200 on the basis of the light beams that have passed through the analyzer 146h. In addition, polarized images based on the light beams that have a plane of polarization the same as that of the linearly polarized light beams emitted from the light emitting units 122v can be acquired from the light beams returned from the subject 200 on the basis of the light beams that have passed through the analyzer 146v. The direction of the transmission axis of the analyzer 146h and the direction of the transmission axes of the polarizers 126 of the light emitting units 122h do not have to be strictly parallel to each other and may differ from each other about several degrees. Likewise, the direction of the transmission axis of the analyzer 146v and the direction of the transmission axes of the polarizers 126 of the light emitting units 122v do not have to be strictly parallel to each other and may differ from each other about several degrees.

Operation of Image Forming Device

An example of the operation of the image forming device 100A will now be described with reference to the drawings. The following describes the case where an image of a human eyeball is formed as the subject 200.

FIG. 3 is a schematic diagram of a typical process performed by an illumination control circuit 162 and an image forming circuit 164. In the observation of the subject 200, the subject 200 is illuminated with first linearly polarized light beams, polarized in a first direction (step S1). For example, at a certain time instant t, the illumination control circuit 162 (see FIG. 1) lights at least two of the multiple light sources 124 in the illuminating device 120A, in front of which the polarizers 126 having the transmission axes oriented in the same direction are disposed, and turns out the rest of the light sources 124. For example, the illumination control circuit 162 selectively lights the light sources 124 in the light emitting units 122h (see FIG. 2). In this case, the illumination light beams polarized in the lateral direction of the drawing are emitted from the two light emitting units 122h to the subject 200.

Figure 4A:
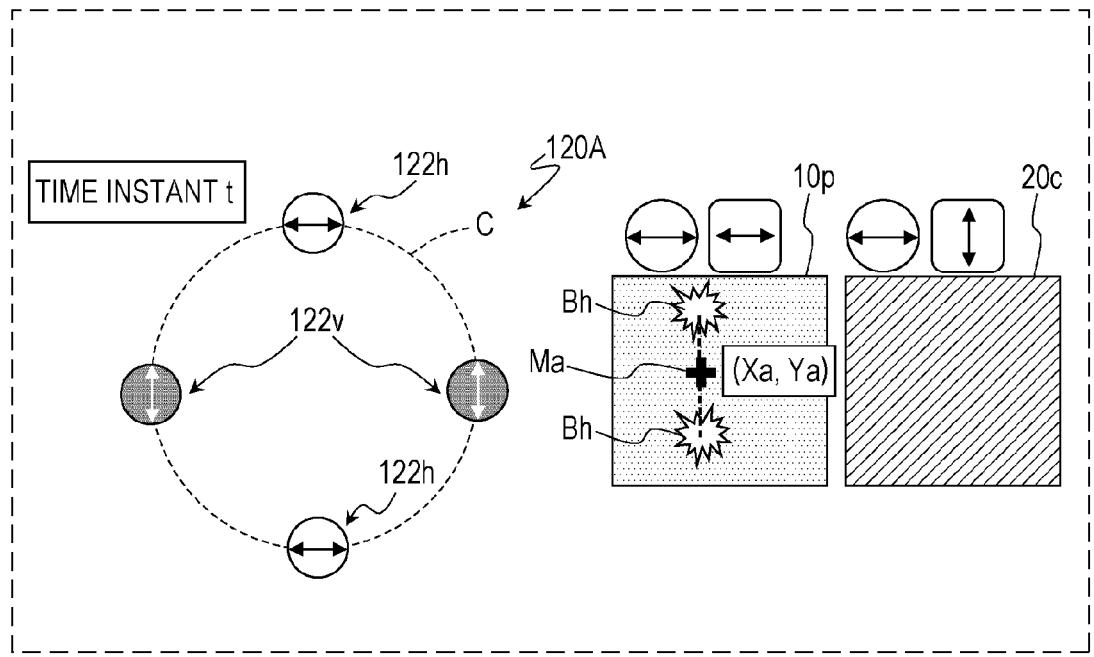
FIG. 4A is a diagram illustrating the operation state of an illuminating device at a certain time instant in combination with polarized images acquired at the time instant.

Subsequently, two polarized images captured from different viewpoints are acquired through illumination with the first linearly polarized light beams (step S2). FIG. 4A is a diagram illustrating the operation state of the illuminating device 120A at a certain time instant tin combination with polarized images 10p and 20c acquired at the time instant t. FIG. 4A illustrates, on the right side, examples of two polarized images 10p and 20c captured by the imaging device 140A when the subject 200 is illuminated with illumination light beams from the light emitting units 122h. The reflection light beams from the subject 200 include a component whose plane of polarization is the same as that of the linearly polarized light beams emitted from the light emitting units 122h and a component whose plane of polarization is the same as that of the linearly polarized light beams emitted from the light emitting units 122v. The polarized image 10p is an image based on, of light beams reflected off the subject 200, light beams that have passed through the analyzer 146h and have been incident on the area Ra of the imaging surface of the image sensor device 142. In other words, the polarized image 10p is an image based on, of light beams returned from the subject 200, light beams whose plane of polarization is the same as that of the linearly polarized light beams emitted from the light emitting units 122h. Here, the transmission axes of the polarizers 126 of the light emitting units 122h and the analyzer 146h are oriented in the same direction, and thus, the polarized image 10p may be referred to as a first parallel nicols image.

When the multiple first light emitting devices, which are the light emitting units 122h, illuminate the subject with first light beams polarized in the first direction during a first period, and the subject reflects the first light beams and outputs first reflection light beams and second reflection light beams, "a first polarizing filter that selectively transmits light beams polarized in the first direction", an example of which is the analyzer 146h, may receive the first reflection light beams and output first polarized light beams, polarized in the first direction.

Multiple first pixels included in the image sensor device 142 may detect the first polarized light beams incident on the area Ra of the imaging surface, and the image sensor device 142 may output a first image having multiple first pixel values of the multiple first pixels, that is, a first parallel nicols image, an example of which is the polarized image 10p.

Mirror reflection negligibly changes the polarization state. The linearly polarized light beams emitted from the light emitting units 122h are reflected as linearly polarized light beams whose plane of polarization is the same as that of the illumination light beams. Thus, as schematically illustrated in FIG. 4A, the polarized image 10p has images Bh of the bright spots BP when linearly polarized light beams emitted from the light emitting units 122h are mirror-reflected off the subject 200. As described above, the position of each bright spotBP on the subject 200 reflects the position of the corresponding light source 124 lit during image capturing. Here, the images Bh of the bright spots BP appear at two positions in the vertical direction of the polarized image 10p. The thick cross in FIG. 4A indicates the centroid Ma of a geometric shape (here, a line segment) defined by the positions of the images Bh of the bright spots BP. The centroid Ma here is a middle point of the line segment connecting the centers of the images Bh of the bright spots BP to each other.

The centroid Ma may be calculated by, for example, the following image processing:

1) The images Bh of the bright spots BP are significantly bright and thus usually have saturated luminance (for example, an 8-bit image has a pixel value of 255). Thus, the above-described areas can be extracted from the image through binarization;

2) The extracted areas are labeled and subjected to noise reduction to extract only two areas; and 3) The coordinates of the centroid are calculated in each of the two areas to finally acquire the centroid Ma through calculation of the coordinates of the centroid for the two areas.

In the case of an n-sided polygon having n vertices, the following may be satisfied: $xg=(\Sigma xi)/N$, and $yg=(\Sigma yi)/N$, where the coordinates of each of the n vertices are (xi, yi), i is a natural number greater than or equal to one and smaller than or equal to N, and the coordinates of the centroid of the n-sided polygon are (xg, yg). The image sensor device 142 may output a first image having multiple first pixel values of the multiple first pixels, that is, a first parallel nicols image, an example of which is the polarized image 10p. The multiple first pixels may include multiple second pixels and multiple third pixels. The multiple first pixel values of the multiple first pixels may include multiple second pixel values of the multiple second pixels and multiple third pixel values of the multiple third pixels. When each of the multiple second pixel values of the multiple second pixels is greater than the corresponding one of the multiple third pixel values of the multiple third pixels, the bright spots BP in the first image may appear at the multiple second pixels.

The imaging device may have a first area including multiple first pixels, including multiple second pixels and multiple third pixels. When the first area is represented with an xy orthogonal coordinate system, the image forming circuit 164 may calculate a first coordinate value (Xa, Ya), indicating the centroid Ma, which is the geometric centroid of multiple coordinates of the multiple second pixels.

On the other hand, the polarized image 20c is an image based on, of light beams reflected off the subject 200, light beams that have passed through the analyzer 146v and that have been incident on the area Rb of the imaging surface of the image sensor device 142. In other words, the polarized image 20c is an image based on, of light beams returned from the subject 200, light beams whose plane of polarization is the same as that of the linearly polarized light beams emitted from the light emitting units 122v. A human eyeball has a cornea having a smooth transparent surface. The illumination light beams emitted from the light emitting units 122h are reflected by or around the surface of the eyeball and do not have their polarization state changed. As is clear from FIG. 2, here, the direction of the transmission axes of the polarizers 126 of the light emitting units 122v is perpendicular to the direction of the transmission axis of the analyzer 146v. Thus, no image Bh of the luminous point BP appears in the polarized image 20c. The polarized image 20c is a dark image having a low contrast ratio. The polarized image 20c may be referred to as a first crossed nicols image.

When multiple first light emitting devices, an example of which is the light emitting units 122h, illuminates the subject with first light beams, polarized in the first direction during the first period, and the subject reflects the first light beams and outputs first reflection light beams and second reflection light beams, "a second polarizing filter that selectively transmits light beams polarized in a second direction", an example of which is the analyzer 146v, may receive the second reflection light beams and output second polarized light beams, polarized in the second direction.

Subsequently, at a time instant (t+1) following the time instant t, the subject 200 is illuminated with second linearly polarized light beams, polarized in the second direction crossing the first direction (step S3 in FIG. 3). For example, the illumination control circuit 162 turns out the light sources 124 of the light emitting units 122h and lights the light sources 124 of the light emitting units 122v. At this time, the two light emitting units 122v illuminate the subject 200 with the illumination light beams polarized in the vertical direction in the drawings. In this manner, the illumination control circuit 162 drives the illuminating device 120A so that the light sources 124, in front of which the polarizers 126 having the transmission axes oriented in the same direction are disposed, are lighted at the same time point and so that the light sources 124, in front of which the polarizers 126 having the transmission axes oriented in different directions are disposed, are lighted at different time points. In this structure, the subject 200 can be sequentially illuminated with linearly polarized light beams whose electric field vector oscillates in a first direction (for example, horizontal direction) and linearly polarized light beams whose electric field vector oscillates in a second direction (for example, vertical direction) crossing the first direction.

Figure 4B:
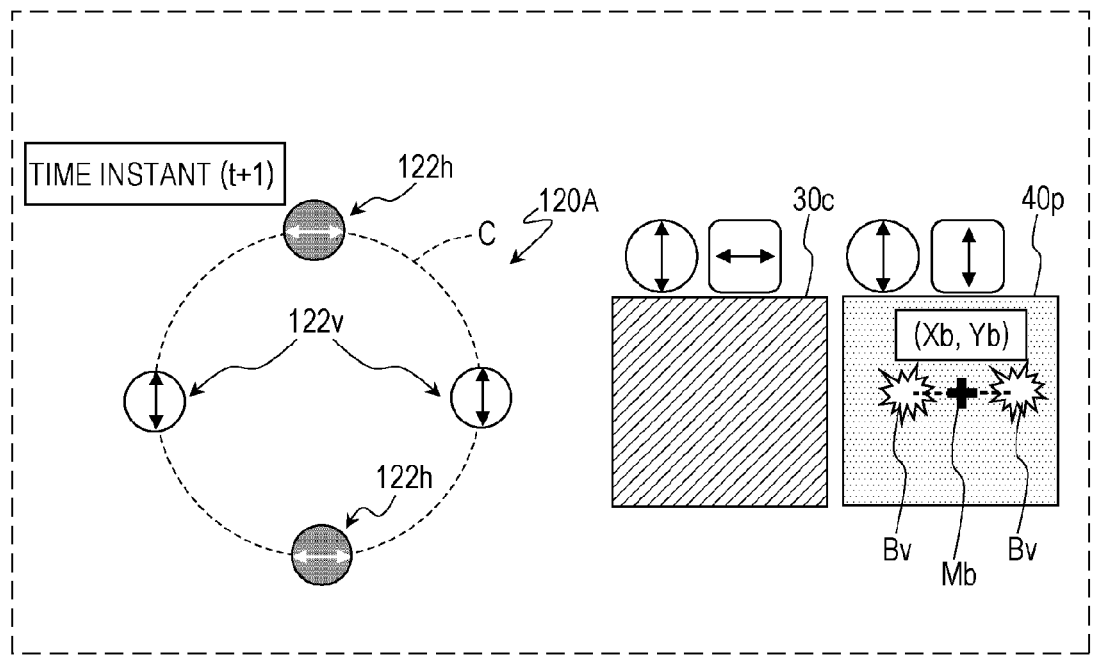
FIG. 4B is a diagram illustrating the operation state of the illuminating device at a time instant subsequent to the certain time instant in combination with polarized images acquired at the subsequent time instant.

Subsequently, two polarized images captured from different viewpoints are acquired through illumination with second linearly polarized light beams (see step S4 in FIG. 3). FIG. 4B is a diagram illustrating the operation state of the illuminating device 120A at a time instant (t+1) in combination with polarized images 30c and 40p acquired at the time instant (t+1). In the state where the light sources 124 in the light emitting units 122v are selectively lighted, the subject 200 is illuminated with illumination light beams polarized in the vertical direction of the drawings. FIG. 4B illustrates, on the right side, examples of two polarized images 30c and 40p captured by the imaging device 140A when the subject 200 is illuminated with illumination light beams from the light emitting units 122v. The polarized image 30c is an image based on, of light beams reflected off the subject 200, light beams that have passed through the analyzer 146h and have been incident on the area Ra of the imaging surface of the image sensor device 142. In other words, the polarized image 30c is an image based on, of light beams returned from the subject 200, light beams whose plane of polarization is the same as that of the linearly polarized light beams emitted from the light emitting units 122h. Similarly to the polarized image 20c (first crossed nicols image), the polarized image 30c is a dark image having a low contrast ratio and no image of the luminous point BP appears in the polarized image 30c. The polarized image 30c may be referred to as a second crossed nicols image.

When multiple second light emitting devices, an example of which is the light emitting units 122v, illuminate the subject with second light beams polarized in the second direction during a second period, different from "the first period in which the multiple first light emitting devices illuminate the subject with first light beams", and the subject reflects the second light beams and outputs third reflection light beams and fourth reflection light beams, "the first polarizing filter that selectively transmits light beams polarized in the first direction", an example of which is the analyzer 146h, may receive the third reflection light beams and output third polarized light beams polarized in the first direction.

Multiple first pixels included in the image sensor device 142 may detect third polarized light beams incident on the area Ra of the imaging surface, and the image sensor device 142 may output a third image including multiple fifth pixel values of the multiple first pixels, that is, a second crossed nicols image, an example of which is the polarized image 30c.

On the other hand, the polarized image 40p is an image based on, of light reflected off the subject 200, light beams that have passed through the analyzer 146v and that have been incident on the area Rb of the imaging surface of the image sensor device 142. In other words, the polarized image 40p is an image based on, of light beams returned from the subject 200, light beams whose plane of polarization is the same as that of the linearly polarized light beams emitted from the light emitting units 122v. The direction of the transmission axes of the polarizers 126 of the light emitting units 122v is parallel to the direction of the transmission axis of the analyzer 146v. The polarized image 40p may be referred to as a second parallel nicols image.

When the multiple second light emitting devices, an example of which is the light emitting units 122v, illuminate the subject with second light beams polarized in the second direction during a second period different from "the first period in which the multiple first light emitting devices illuminate the subject with first light beams", and the subject reflects the second light beams and outputs third reflection light beams and fourth reflection light beams, "a second polarizing filter that selectively transmits light beams polarized in the second direction", an example of which is the analyzer 146v, may receive the fourth reflection light beam and output a fourth polarized light beam, polarized in the second direction.

Multiple second pixels included in the image sensor device 142 may detect the fourth polarized light beams incident on the area Rb of the imaging surface, and the image sensor device 142 may output a fourth image having multiple sixth pixel values of the multiple fourth pixels, that is, output a second parallel nicols image, an example of which is the polarized image 40p.

As schematically illustrated on the right side of FIG. 4B, the polarized image 40p has images By of bright spots BP when linearly polarized light beams emitted from the light emitting units 122v are mirror-reflected off the subject 200. The images By of the bright spots BP appear at two positions of the polarized image 40p in the lateral direction of the polarized image 40p corresponding to the arrangement of the light emitting units 122v. The thick cross in FIG. 4B indicates the centroid Mb of a geometric shape (here, a line segment) defined by the positions of the images By of the bright spots BP. The centroid Mb here is a middle point of the line segment connecting the centers of the images By of the bright spots BP to each other.

The image sensor device 142 may output a fourth image having multiple sixth pixel values of the multiple fourth pixels, that is, a second parallel nicols image, an example of which is the polarized image 40p. The multiple fourth pixels may include multiple fifth pixels and multiple sixth pixels. The multiple sixth pixel values of the multiple fourth pixels may include multiple seventh pixel values of the multiple fifth pixels and multiple eighth pixel values of the multiple sixth pixels. When each of the multiple seventh pixel values of the multiple fifth pixels is greater than the corresponding one of the multiple eighth pixel values of the multiple sixth pixels, the bright spots BP included in the fourth image may appear on multiple seventh pixels.

The imaging device may include a second area including multiple fourth pixels, including multiple fifth pixels and multiple sixth pixels. When the second area is represented with an xy orthogonal coordinate system, the image forming circuit 164 may calculate a second coordinate value (Xb, Yb), indicating the centroid Mb, which is the geometric centroid of the coordinates of the multiple fifth pixels.

The polarized image 10p illustrated in FIG. 4A and the polarized image 30c illustrated in FIG. 4B are images captured from the same viewpoint. Thus, the polarized images 10p and 30c do not have parallax between each other unless the arrangement between the subject 200 and the image forming device 100A is changed between the time instant t and the time instant (t+1). Similarly, the polarized image 20c illustrated in FIG. 4A and the polarized image 40p illustrated in FIG. 4B do not have parallax between each other. However, the polarized images 10p and 20c illustrated in FIG. 4A have parallax between each other and the polarized images 30c and 40p illustrated in FIG. 4B have parallax between each other. When the coordinates of the centroid Ma in the polarized image 10p are (Xa, Ya) and the coordinates of the centroid Mb in the polarized image 40p are (Xb, Yb), their x-coordinates do not coincide with each other. As described below, the parallax correction unit 164a (see FIG. 1) performs correction to cancel the effect of such a viewpoint difference.

In parallax correction, the parallax correction unit 164a firstly calculates the centroid Ma of the images Bh in the polarized image 10p (first parallel nicols image) and the centroid Mb of the images By in the polarized image 40p (second parallel nicols image) (step S5 in FIG. 3). Examples usable as the coordinates of each image Bh or the coordinates of each image By include the coordinates of a pixel positioned at the center of multiple pixels having a pixel value higher than a predetermined threshold value. Normally, the images Bh and By have significantly high luminance and thus have saturated pixel values. Since each of the polarized images 10p and 40p does not have other high-luminance pixel areas, the image can be uniquely distinguished and determined in each polarized image, so that the coordinates of the center (geometric centroid) of such pixels can be easily acquired.

Subsequently, the parallax correction unit 164a translates each polarized image so that the calculated coordinates of the centroid coincides with the appropriate intended coordinates (step S6). Here, the reason why the correction completes with mere translation is because, in the present disclosure, the parallax is a deviation in only the horizontal direction (laterally) since the apertures APh and APv (viewpoints) are disposed parallel to each other in the lateral direction. FIGS. 5A and 5B are diagrams illustrating an example of parallax correction performed by the parallax correction unit 164a. FIG. 5A schematically illustrates the state before parallax correction. As schematically illustrated in FIG. 5A, when the viewpoint from which the polarized image 10p is captured and the viewpoint from which the polarized image 40p is captured differ from each other in, for example, the horizontal direction, the x-coordinate of the centroid Ma does not coincide with the x-coordinate of the centroid Mb. That is, Xa≠Xb.

The parallax correction unit 164a translates the polarized image 10p so that the coordinates of the centroid Ma coincide with the appropriate intended coordinates. For example, as schematically illustrated with a thick arrow A1 in FIG. 5A, the parallax correction unit 164a translates the polarized image 10p to have the centroid Ma positioned at the center of the image area. For example, the polarized image 10*p* may be translated to have the centroid Ma positioned on the perpendicular line passing through the center of the polarized image 10*p*. As schematically illustrated with a thick arrow A4, the parallax correction unit 164*a* translates the polarized image 40*p* to have the centroid Mb positioned at the center of the image area. For example, the polarized image 40*p* may be translated to have the centroid Mb positioned on the perpendicular line passing through the center of the polarized image 40*p*. Translating each polarized image in this manner cancels the parallax between the polarized images 10*p* and 40*p*.

As schematically illustrated with a thick arrow A3 in FIG. 5A, the parallax correction unit 164*a* also translates the polarized image 30*c*, in the same manner as the polarized image 10*p*. The distance by which and the direction in which the polarized image 30*c* is translated at this time coincide with the distance by which and the direction in which the polarized image 10*p* is translated. Such translation can cancel the parallax between the polarized images 30*c* and 40*p* after image capturing. As schematically illustrated with a thick arrow A2 in FIG. 5A, the parallax correction unit 164*a* translates the polarized image 20*c* in the same manner as the polarized image 40*p*. Specifically, the polarized image 20*c* is translated by a distance the same as the distance by which and in a direction the same as the direction in which the polarized image 40*p* is translated. Such translation can cancel the parallax between the polarized images 20*c* and 10*p* after image capturing. Consequently, parallax between four polarized images acquired from two types of linearly polarized light beams emitted to the subject 200 and from two viewpoints is cancelled, and images similar to four polarized images (two parallel nicols images and two crossed nicols images) captured from the same viewpoint can be acquired.

FIG. 5B schematically illustrates the state after parallax correction. Polarized images 10*pt* and 30*ct* illustrated in FIG. 5B are images resulting from the translation based on the positions of the images Bh of multiple bright spots that appear on the polarized image 10*p*. Polarized images 20*ct* and 40*pt* are images resulting from the translation based on the positions of the images By of multiple bright spots that appear on the polarized image 40*p*. In FIG. 5B, asterisk Ctr in each of these images indicates the center of the image area before translation. After the translation, each of these polarized images has, at its end portion, a blank area BK having no image data of the subject 200. To form a final image of the subject 200, the pixel values of the pixels in the blank area BK may be discarded without being used.

In this manner, in a typical embodiment of the present disclosure, bright spots BP are propulsively formed on the subject 200 to cancel the effect of parallax between multiple polarized images using the positions of the images of the bright spots BP that appear in a parallel nicols image. This method enables cancellation of the effect of parallax after the polarized images are acquired. Thus, the result is similar to that obtained in the case where parallel nicols images and crossed nicols images are captured from a single viewpoint. When switching of linearly polarized light beams with which the subject 200 is illuminated and image capturing during illumination with each linearly polarized light beam are performed at a fast speed, multiple polarized images acquired through illumination with illumination light beams having different polarization states can have simultaneity. In other words, such operations enable acquiring of the result similar to that obtained in the case where two parallel nicols images and two crossed nicols images are simultaneously captured from a single viewpoint from illumination light beams having different polarization states.

The image processing unit 164*b* (see FIG. 1) generates image data of the subject 200 on the basis of the translated polarized images 10*pt*, 20*ct*, 30*ct*, and 40*pt*. An example of the process performed by the image processing unit 164*b* will now be described.

FIG. 6 is a schematic diagram of a typical process performed by an image processing unit 164*b*.

First, the image processing unit 164*b* that has received image data of the translated polarized images 10*pt*, 20*ct*, 30*ct*, and 40*pt* from the parallax correction unit 164*a* generates an average parallel nicols image from two parallel nicols images subjected to the parallax correction and an average crossed nicols image from two crossed nicols images subjected to the parallax correction (see step S7 in FIG. 3). As schematically illustrated in FIG. 6, the image processing unit 164*b* generates an average parallel nicols image 50*ta* from the polarized images 10*pt* and 40*pt* subjected to the parallax correction. The pixel value of each pixel of the average parallel nicols image 50*ta* is calculated as an arithmetic mean of the pixel values of the corresponding pixels of the polarized images 10*pt* and 40*pt*. The image processing unit 164*b* generates an average crossed nicols image 60*ta* whose pixel value of each pixel is an arithmetic mean of the pixel values of the corresponding pixels of the polarized images 20*ct* and 30*ct*.

The image processing unit 164*b* then calculates a difference between the average parallel nicols image 50*ta* and the average crossed nicols image 60*ta* to generate a polarized subtracted image 70 (step S8 in FIG. 3). This subtraction forms the image of the subject 200 into the averaged polarized subtracted image 70. The averaged polarized subtracted image 70 can be effectively used to detect, for example, a foreign substance or scratch on the cornea. Typically, the images of the bright spots BP remain on the averaged polarized subtracted image 70, but these images of the bright spots BP do not significantly hinder the observation of the cornea. For ease of illustration, FIGS. 4A, 4B, and 6 merely illustrate the images of the bright spots BP in an exaggerated enlarged manner.

Here, the lateral direction in the drawing is represented as 0°, and an image based on light beams that have passed through an analyzer, whose transmission axis is oriented at an angle β with respect to the lateral direction of the drawing, formed through illumination with illumination light beams having an plane of polarization of an angle α is represented as LαCβ. In this case, the averaged polarized subtracted image 70 can be expressed as {L0C0+L90C90}/2−{L0C90+L90C0}/2, which can be transformed into {L0C0−L0C90}/2+{L90C90−L90C0}/2. It seems that, instead of the above procedure, the same result as the averaged polarized subtracted image 70 can be also acquired by the following procedure: the difference between the parallel nicols image and the crossed nicols image acquired through illumination with first linearly polarized light beams and the difference between the parallel nicols image and the crossed nicols image acquired through illumination with second linearly polarized light beams are calculated first, and these differences are then subjected to averaging to acquire the result. However, this procedure leaves, in a final image, the effect of, for example, an optical path difference attributable to the difference of the viewpoints from which the parallel nicols image and the crossed nicols image are acquired. On the other hand, as schematically illustrated in FIG. 6, the processing for calculating the average parallel nicols image and the average crossed nicols image includes subtraction using the results obtained by averaging two images having different polarization or viewpoints during image capturing. Thus, the image quality difference attributable to the difference in polarization or viewpoint during image capturing can be reduced.

The image sensor device 142 may detect, at multiple first pixels included in the image sensor device 142, first polarized light beams that have been incident on the area Ra of the imaging surface, and output a first image having multiple first pixel values of the multiple first pixels, that is, a first parallel nicols image, an example of which is the polarized image 10p. The image sensor device 142 may detect, at multiple second pixels included in the image sensor device 142, second polarized light beams that have been incident on the area Rb of the imaging surface, and output a second image having multiple fourth pixel values of the multiple fourth pixels, that is, a first crossed nicols image, an example of which is the polarized image 20c. The image sensor device 142 may detect, at multiple first pixels included in the image sensor device 142, third polarized light beams that have been incident on the area Ra of the imaging surface, and output a third image having multiple fifth pixel values of the multiple first pixels, that is, a second crossed nicols image, an example of which is the polarized image 30c. The image sensor device 142 may detect, at multiple second pixels included in the image sensor device 142, fourth polarized light beams that have been incident on the area Rb of the imaging surface, and output a fourth image having multiple sixth pixel values of the multiple fourth pixels, that is, a second parallel nicols image, an example of which is the polarized image 40p. The image sensor device 142 may include a first area, which includes multiple first pixels including multiple second pixels and multiple third pixels, and a second area, which includes multiple fourth pixels including multiple fifth pixels and multiple sixth pixels.

In this case, the first area and the second area may be represented with xy orthogonal coordinates.

The image forming circuit 164 may calculate a first coordinate value (Xa, Ya), representing the geometric centroid of the coordinates of multiple second pixels, and a second coordinate value (Xb, Yb), representing the geometric centroid of the coordinates of multiple fifth pixels. When, of pixel values of a first image, a pixel value of the pixel at the coordinates (x, y) included in multiple first pixels is determined as I1, the image forming circuit 164 may calculate x'=x−Xa−p and y'=y−Ya−q and may determine the pixel value at the coordinates (x', y') as I1. When, of pixel values of a second image, a pixel value of the pixel at the coordinates (x, y) included in multiple fourth pixels is determined as I2, the image forming circuit 164 may calculate x'=x−Xb−p and y'=y−Yb−q and may determine the pixel value at the coordinates (x', y') as I2. When, of pixel values of a third image, a pixel value of the pixel at the coordinates (x, y) included in multiple first pixels is determined as I3, the image forming circuit 164 may calculate x'=x−Xa−p and y'=y−Ya−q and may determine the pixel value at the coordinates (x', y') as I3. When, of pixel values of a fourth image, a pixel value of the pixel at the coordinates (x, y) included in multiple fourth pixels is determined as I4, the image forming circuit 164 may calculate x'=x−Xb−p and y'=y−Yb−q and may determine the pixel value at the coordinates (x', y') as I4. Here, p and q may be any real numbers. The image forming circuit 164 may calculate the pixel value Ii at the coordinates (xi, yi) as {I1(x'=xi, y'=yi)+I4(x'=xi, y'=yi)}/2−{I2(x'=xi, y'=yi)+I3(x'=xi, y'=yi)}/2. Here, i may be a natural number.

The processing described above with reference to FIG. 6 (hereinafter also referred to as "averaged polarization subtraction" for simplicity) can acquire, in the form of the averaged subtracted polarized image 70, an image data having an enhanced contrast attributable to fine projections and depressions on the surface of the subject 200. The processing can thus acquire usable information on, for example, a scratch or foreign substance on the subject 200 on the basis of the averaged subtracted polarized image 70. The averaged polarization subtraction is particularly effective for observing a subject having a spherical shape and a transparent surface, such as a human eyeball. The following describes this point.

Figure 7:
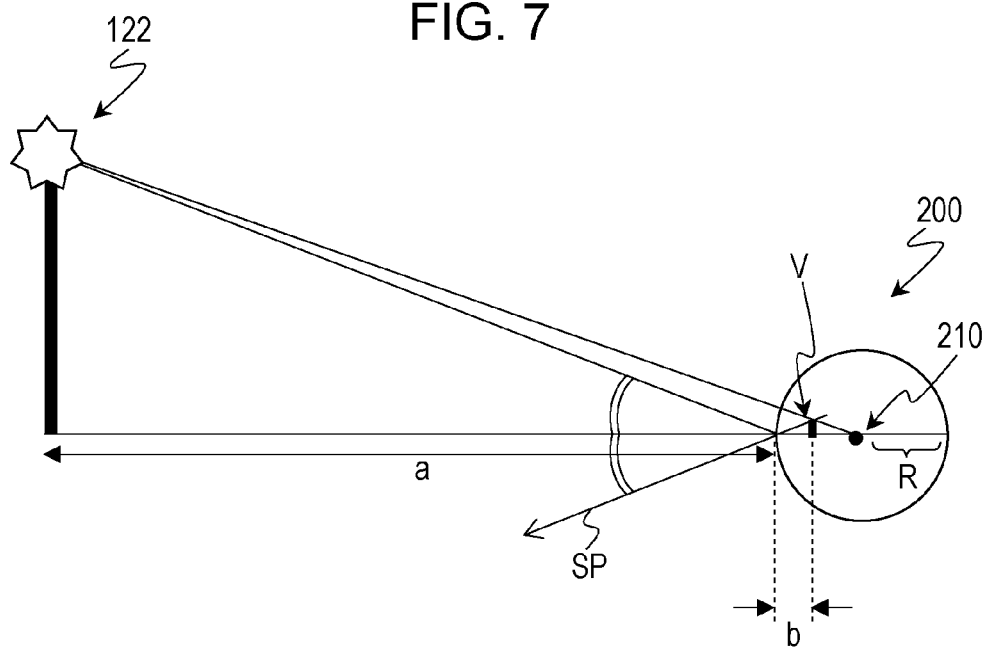
FIG. 7 is a schematic diagram of a positional relationship between the surface of a subject and a virtual image of a light beam emitted from the light emitting unit.

FIG. 7 is a schematic diagram of a positional relationship between the surface of the subject 200 and a virtual image of a light beam emitted from the light emitting unit 122. Here, a human eyeball is regarded as a mirror reflective sphere, and the subject 200 approximates to a convex mirror having a radius R. Here, a case is assumed where the distance between the surface of the subject 200 and the illuminating device 120A is denoted with a and a light emitting unit 122 of the illuminating device 120A illuminates the subject 200 with a light beam. At this time, a virtual image V of the light beam emitted from the light emitting unit 122 is formed at a point of intersection between the line segment connecting the center 210 of the subject 200 and the light emitting unit 122 and an extended line of the arrow SP, representing a light beam mirror-reflected off the surface of the subject 200. As is clear from FIG. 7, the virtual image V is located on the inner side from the surface of the subject 200. When the focal length of the subject 200 approximating to a convex mirror is denoted with f and the distance between the surface of the convex mirror and the image V is denoted with b, the relational expression expressed with formula (1) below holds true.

$$\frac{1}{a} + \frac{1}{-b} = \frac{1}{-f} = \frac{1}{\frac{-R}{2}} \qquad (1)$$

For example, b=3.63 mm when a=200 mm and R=7.4 mm. Specifically, the virtual image V of a light beam emitted from the light emitting unit 122 is not located on the surface of the subject 200 and, precisely speaking, is located at the point 203.63 mm from the illuminating device 120A. The inventors have found that the correction performed in the assumption that the bright spots BP (see FIG. 1) are located on the surface of the subject 200 sometimes fails to fully cancel the effect of the parallax.

Figure 8:
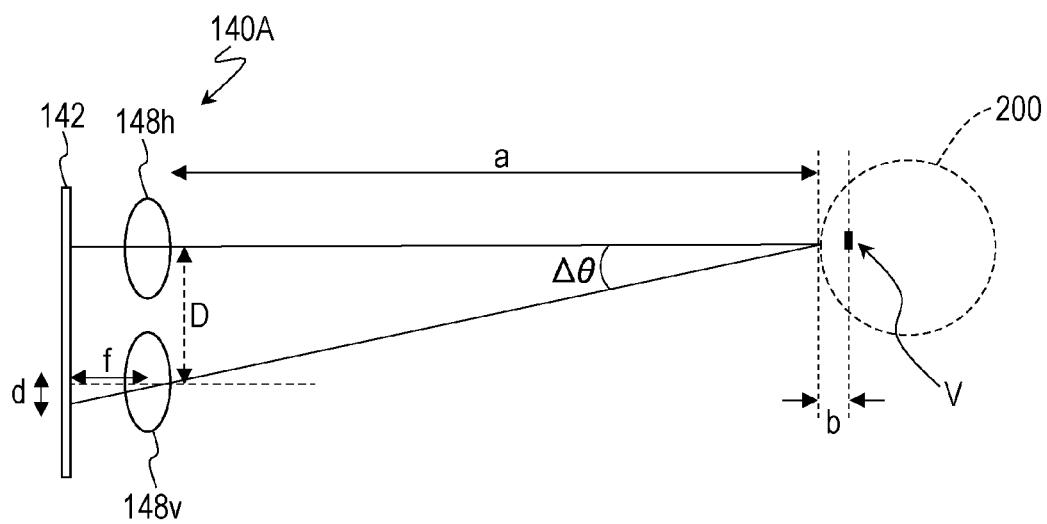
FIG. 8 is a diagram illustrating the relationship between the distance from the surface of the subject to the virtual image and the degree of a deviation of an image formation position on the imaging surface of an image sensor device.

With reference to FIG. 8, the relationship between the distance from the surface of the subject 200 to the virtual image V and the degree of a deviation of an image formation position on the imaging surface of the image sensor device 142 is described. In the schematic arrangement illustrated in FIG. 8, the distance from the subject 200 to the imaging device 140A is regarded as being equal to the distance a between the surface of the subject 200 to the illuminating device 120A. The focal length of the objective lenses 148h and 148v is denoted with f, the angle formed between the line segment connecting the image V and the center of the objective lens 148h together and the line segment connecting the image V and the center of the objective lens 148v together is denoted with Δθ, and the arrangement pitch of image capturing cells of the image sensor device 142 is denoted with P. When the distance a is fully greater than the distance D between the centers of the objective lenses 148*h* and 148*v*, the degree d of the difference of the image formation position is expressed with formula (2), below.

$$d = f \cdot \Delta \frac{\theta}{P} \approx f \cdot \frac{D}{a \cdot P} \qquad (2)$$

In formula (2), d=4.09 when D=1.2 mm, f=1.5 mm, P=2.2 µm, and a=200 mm. This means that two viewpoints have a difference in the image formation position therebetween equivalent to the size of 4.09 image-capturing cells when the virtual image V is assumed to be positioned on the surface of the subject 200. In other words, when the virtual image V is assumed to be positioned on the surface of the subject 200, the size of the parallax between the parallel nicols image and the crossed nicols image corresponds to 4.09 pixels, when converted into the number of pixels. On the other hand, d=4.00 when formula (2) uses a=203.63 mm, corresponding to the actual position of the virtual image V. Specifically, the degree d of the difference differs by 0.09 pixels between the case where the virtual image V is assumed to be located on the surface of the subject 200 and the case where the position calculated on the basis of geometrical optics is used as the position of the virtual image V.

This degree of the difference is less than 1 pixel, which is low. Nevertheless, this difference can lower the accuracy of, for example, surface observation in the processing of simply calculating the difference between a parallel nicols image and a crossed nicols image. From the viewpoint of precise surface observation, lowering the effect of the difference is thus beneficial.

In the above-described operation example, the average parallel nicols image 50*ta* and the average crossed nicols image 60*ta* are calculated, and the averaged subtracted polarized image 70 is acquired from the difference between the average parallel nicols image 50*ta* and the average crossed nicols image 60*ta*. As described above, the average parallel nicols image 50*ta* can be acquired by averaging the images obtained by translating the two parallel nicols images 10*p* and 40*p* acquired from different viewpoints. Thus, the difference between the two parallel nicols images equivalent to, for example, 0.09 pixels attributable to the virtual image V deviating from the original position is spatially averaged in the process of calculating the average parallel nicols image 50*ta*. Similarly, the difference between the translated two crossed nicols images 20*ct* and 30*ct* equivalent to, for example, 0.09 pixels is also spatially averaged in the process of calculating the average crossed nicols image 60*ta*. Specifically, the averaged polarization subtraction can reduce the effect of the parallax attributable to the virtual image V deviating from the original position, on the image obtained as the image of the subject 200.

In this manner, a typical embodiment of the present disclosure can cancel large parallax attributable to the difference between viewpoints from which parallel nicols images and crossed nicols images are captured on the basis of the images of bright spots that appear in each parallel nicols image. In a typical embodiment of the present disclosure, by cancelling large parallax between multiple polarized images, the parallax between polarized images attributable to the difference between viewpoints from which the images are captured can be reduced to less than 1 pixel, when converted into the number of pixels. The averaged polarization subtraction can thus be effectively exerted on multiple polarized images. Performing averaged polarization subtraction after cancelling of the large parallax can thus reduce the effect on parallax attributable to a virtual image of illumination light beams deviating from the original position. Specifically, a typical embodiment of the present disclosure enables more precise surface observation of a subject having, for example, a spherical shape.

The above-described functions of the illumination control circuit 162 and the image forming circuit 164 may be implemented by a combination of a general-purpose processing circuit and software or implemented by hardware specially designed for such processing. In the operation described with reference to FIG. 3, illumination light beams having different planes of polarization may be emitted in any order and image capturing (steps S1 to S4) may be repeated while illumination light beams having different planes of polarization are emitted in different orders.

Figure 9:
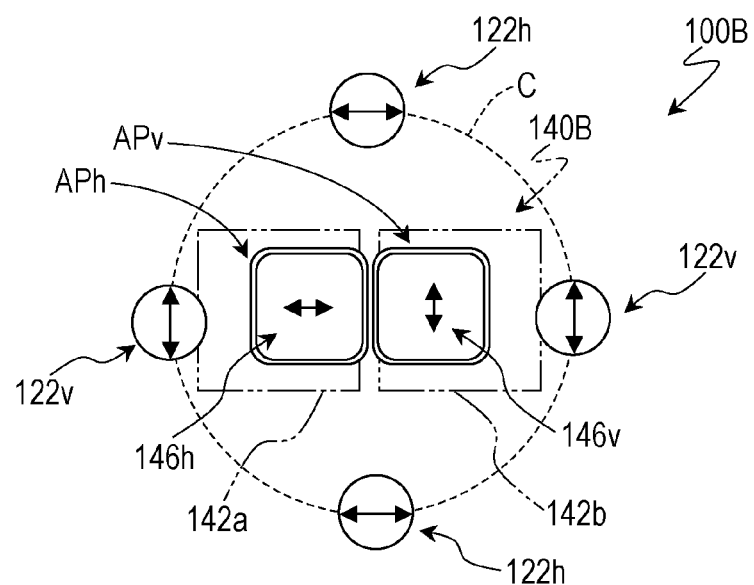
FIG. 9 is a diagram of an example of an image forming device including multiple image sensor devices arranged in correspondence with multiple viewpoints.

FIG. 1 illustrates, by way of example, a structure in which a single image sensor device 142 acquires image signals based on light beams polarized in a certain state and image signals based on light beams polarized in another state. However, the imaging device 140A may include more than one image sensor device. As illustrated in FIG. 9 by way of example, multiple image sensor devices may be arranged corresponding to multiple viewpoints. An image forming device 100B illustrated in FIG. 9 includes a first image sensor device 142*a*, which receives light beams that have passed through the analyzer 146*h* arranged in the aperture APh, and a second image sensor device 142*b*, which receives light beams that have passed through the analyzer 146*v* arranged in the aperture APv. In this structure, the entire area of the imaging surfaces of the image sensor devices 142*a* and 142*b* forms an imaging surface of an imaging device 140B of the image forming device 100B. The imaging surface of the image sensor device 142*a* serves as the area Ra that receives light beams that have passed through the analyzer 146*h*. The imaging surface of the image sensor device 142*b* serves as the area Rb that receives light beams that have passed through the analyzer 146*v*.

In this structure, the image sensor device 142*a* can separately acquire image signals based on light beams that have passed through the analyzer 146*h*, and the image sensor device 142*b* can separately acquire image signals based on light beams that have passed through the analyzer 146*v*. This structure can also effectively use the above-described averaged polarization subtraction. In the process of averaging, the difference between two parallel nicols images and the difference between two crossed nicols images, attributable to a virtual image of illumination light beams deviating from the original position, are spatially averaged. The averaged polarization subtraction can be also used to average the effect of the characteristic difference (for example, the image quality difference) between the image sensor devices 142*a* and 142*b*.

In the above-described embodiment, the coordinates of the centroid of the image Bh and the coordinates of the centroid of the image By are calculated on the basis of the patterns of the images Bh and By of the bright spots BP, which appear in the polarized images acquired at different time instants. Using these coordinate values, the x-coordinates between the multiple polarized images are aligned with each other. However, the processing of the image forming device of the present disclosure is not limited to the above-described processing. For example, processing to cause the multiple polarized images to have the same x-coordinate and the same y-coordinate may be performed. As needed, instead of or in addition to translation, the polarized images may be subjected to another operation (for example, rotation) on the basis of the patterns of the images Bh and By of the bright spots BP that appear in the polarized images. As described below, the illuminating device and the imaging device of the image forming device can also be modified in various manners.

Modification 1

Figure 10:
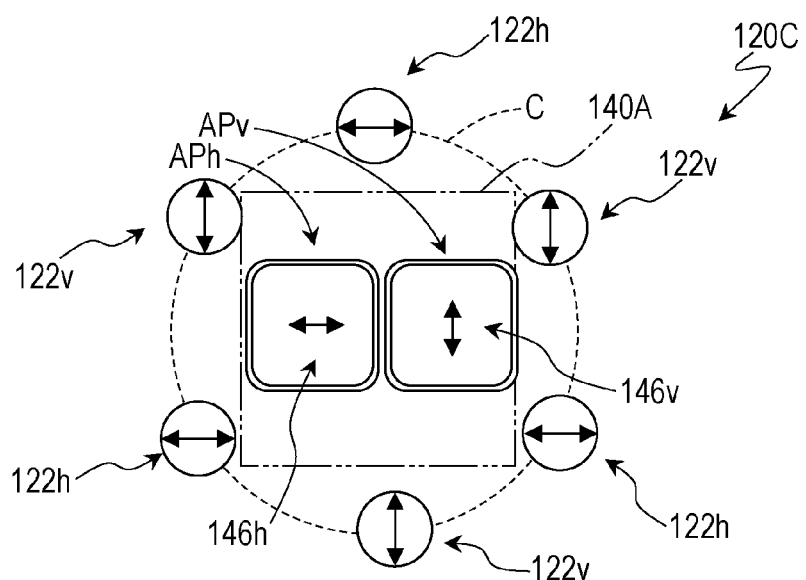
FIG. 10 is a diagram of another example of an arrangement of multiple light emitting units.

FIG. 10 illustrates another example of the arrangement of the multiple light emitting units 122h and 122v. An illuminating device 120C illustrated in FIG. 10 includes three light emitting units 122h and three light emitting units 122v, arranged in a circle. In the example illustrated in FIG. 10, the light emitting units 122h and 122v are alternately arranged at positions 60° rotated apart from each other on the circumference of a virtual circle C drawn with a broken line. In other words, in this example, the light emitting units 122h and 122v are arranged at the positions corresponding to the vertices of a regular hexagon. Also in this example, as in the example illustrated with reference to FIG. 2, the centroid of a geometric shape (here, a regular triangle) connecting the positions of the multiple light emitting units 122h coincides with the centroid of a geometric shape (here, a regular triangle) connecting the positions of the multiple light emitting units 122v. In this example, the centroid of a circle (here, the center of the circle) passing the positions of the multiple light emitting units 122h coincides with the centroid of a circle (here, the center of the circle) passing the positions of the multiple light emitting units 122v.

At a certain time point, the control circuit 160 (see FIG. 1) selectively lights the light sources 124 of the three light emitting units 122h to acquire first parallel nicols images and first crossed nicols images using the imaging device 140A through illumination with first linearly polarized light beams. At another time point, the control circuit 160 selectively lights the light sources 124 of the three light emitting units 122v to acquire second parallel nicols images and second crossed nicols images using the imaging device 140A through illumination with second linearly polarized light beams.

Figure 11A:
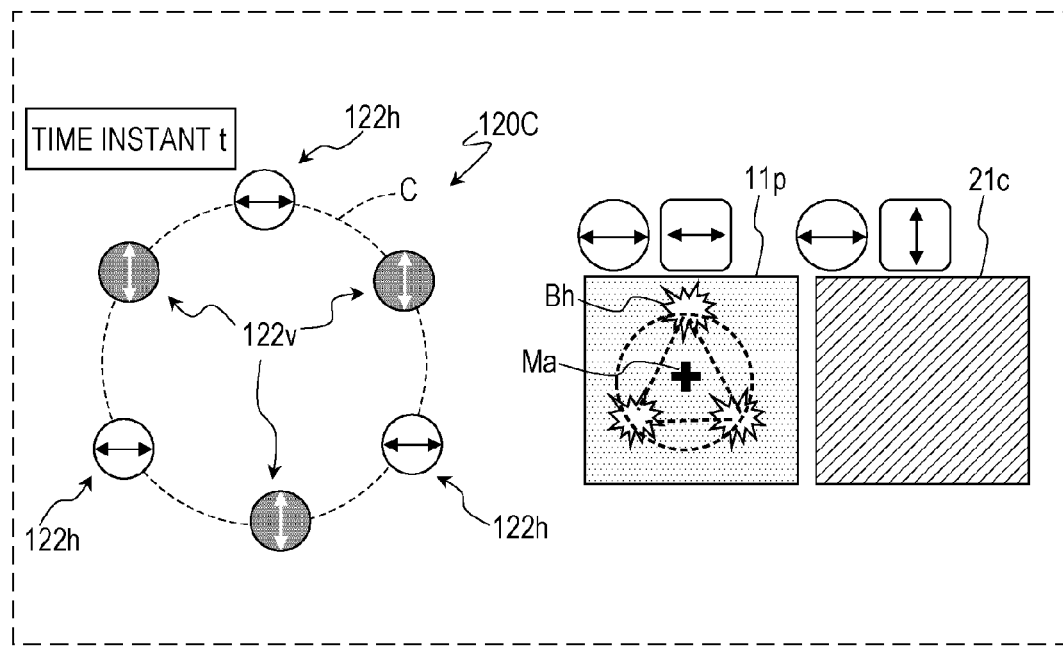
FIG. 11A is a diagram of the operation state of an illuminating device at a certain time instant in combination with polarized images acquired at the time instant.

FIG. 11A is a diagram of the operation state of the illuminating device 120C at a certain time instant t in combination with polarized images 11p and 21c acquired at the time instant t. When image capturing is performed while the light sources 124 of the light emitting units 122h are selectively lighted, images Bh of three bright spots appear in the polarized image 11p, serving as a first parallel nicols image, corresponding to the three light emitting units 122h, as schematically illustrated on the right side of FIG. 11A. Thus, a triangle having vertices at the centers of the images Bh or a circle passing through the centers of the images Bh can be assumed, and the coordinates of the centroid of the triangle or circle can be calculated from the positions of these images Bh in the polarized image 11p. A thick cross in FIG. 11A indicates the centroid Ma of a geometric shape (here, a triangle or circle) defined by the positions of the images Bh of the bright spots BP.

Figure 11B:
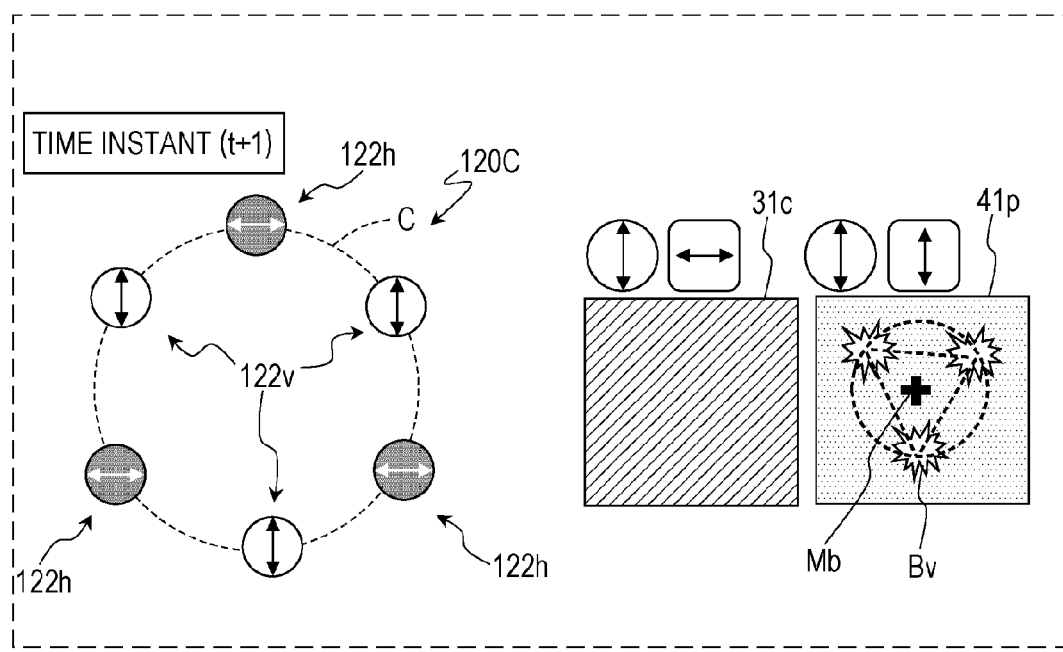
FIG. 11B is a diagram of the operation state of the illuminating device at a subsequent time instant in combination with polarized images acquired at the subsequent time instant.

FIG. 11B is a diagram of the operation state of the illuminating device 120C at a time instant (t+1) in combination with polarized images 31c and 41p acquired at the time instant (t+1). When image capturing is performed while the light sources 124 of the light emitting units 122v are selectively lighted, images By of three bright spots appear in the polarized image 41p, serving as a second parallel nicols image, corresponding to the three light emitting units 122v, as schematically illustrated on the right side of FIG. 11B. A thick cross in FIG. 11B indicates the centroid Mb of a geometric shape (here, a triangle or circle) defined by the positions of the images By of the bright spots BP.

In this example, the centers of the three light emitting units 122h located at the positions 120° rotated apart from each other on the circle C and the centers of the three light emitting units 122v located at the positions 120° rotated apart from each other, which are 60° apart from the positions of the respective light emitting units 122h, are located at the vertices of regular triangles. These regular triangles have the same centroid. When the subject 200 is illuminated in a direction approximately perpendicular to the surface of the subject 200, the centroid Ma of a geometric shape defined by the positions of the images Bh in the polarized image 11p can be said as coinciding with the centroid Mb of a geometric shape defined by the positions of the images By in the polarized image 41p if the polarized images have no parallax between each other. As described with reference to FIGS. 5A and 5B, when the polarized image 11p and the polarized image 41p are respectively translated so that the coordinates of the centroid Ma and the coordinates of the centroid Mb coincide with appropriate intended coordinates (such as the center of the image area), the parallax between these polarized image can be cancelled. In addition, when the polarized image 31c is translated in the same manner as the polarized image 11p and the polarized image 21c is translated in the same manner as the polarized image 41p, the parallax between the four polarized images can be cancelled. The translation at this time is not limited to the movement in the X direction and may be a combination of a movement in the X direction and a movement in the Y direction. The translated four polarized images may be subjected to the above-described averaged polarization subtraction.

In this manner, an increase in number of light emitting units controlled to concurrently emit illumination light beams can increase the number of images of bright spots that appear in a parallel nicols image. The increase in number of the images of the bright spots that appear in the parallel nicols image can increase the amount of information usable to calculate the coordinates used for translating the polarized image (for example, the coordinates of the centroid of a geometric shape defined by the positions of the images of the bright spots), so that an enhancement of parallax correction accuracy can be expected. As illustrated in FIGS. 11A and 11B, in the case where three images of the bright spots appear in a parallel nicols image, instead of the centroid of a triangle having vertices at the positions of the images of the bright spots, the coordinates of, for example, the inner center or the circumcenter may be used to translate the polarized image. Alternatively, the center of a circle passing through the positions of the images of three bright spots may be calculated from the positions of the images and used to translate the polarized image.

Modification Example 2

Figure 12:
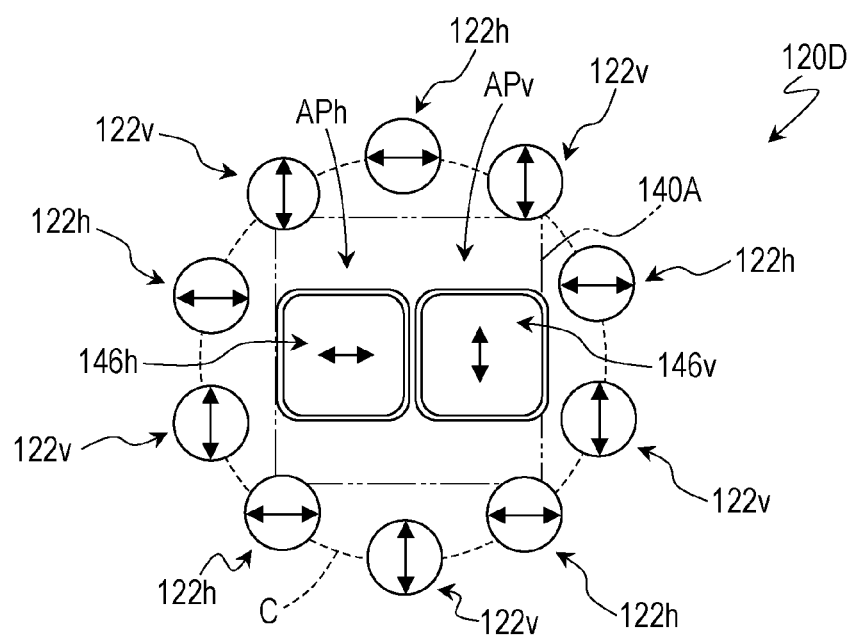
FIG. 12 is a diagram of another example of an arrangement of the multiple light emitting units.

FIG. 12 is a diagram of another example of an arrangement of the multiple light emitting units 122h and 122v. An illuminating device 120D illustrated in FIG. 12 includes five light emitting units 122h and five light emitting units 122v arranged in a circle. In this example, the light emitting units 122h and 122v are alternately arranged at positions 36° rotated apart from each other on a virtual circle C drawn with a broken line. The illumination control circuit 162 may control the illuminating device 120D in the same manner as the example described thus far.

Figure 13A:
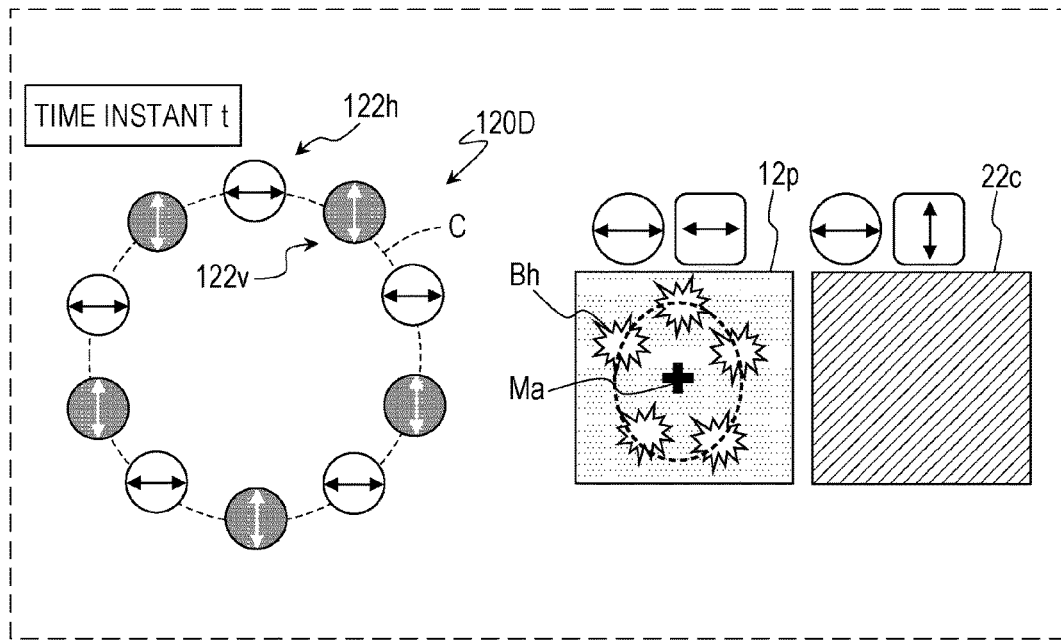
FIG. 13A is a diagram of the operation state of an illuminating device at a certain time instant in combination with polarized images acquired at the time instant.
Figure 13B:
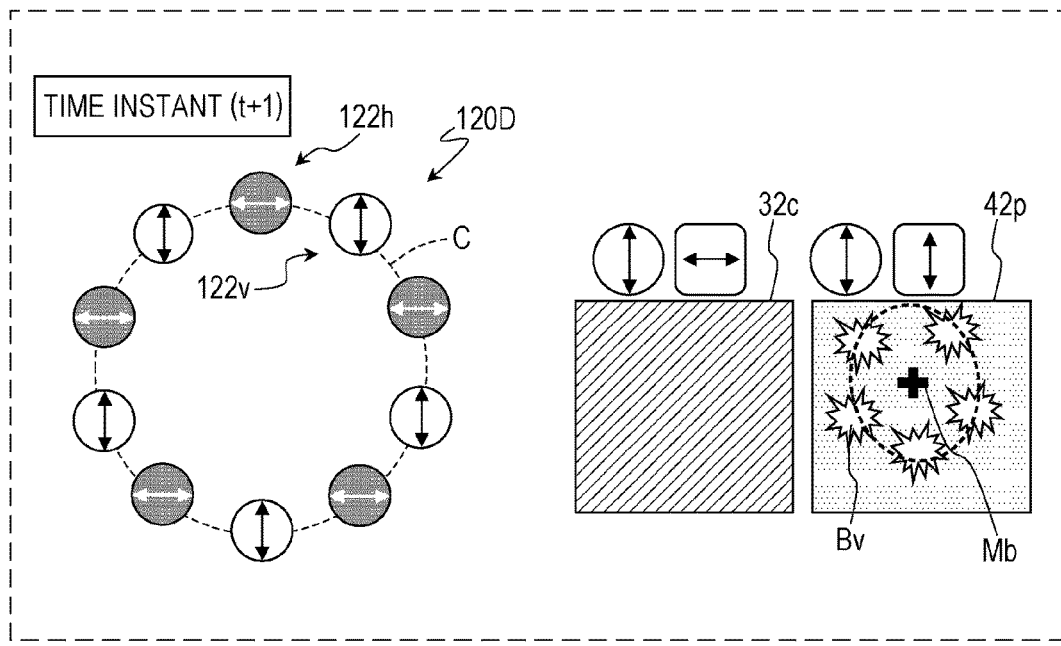
FIG. 13B is a diagram of the operation state of an illuminating device at the subsequent time instant in combination with polarized images acquired at the subsequent time instant.

FIG. 13A is a diagram of the operation state of the illuminating device 120D at a time instant t in combination with polarized images 12p and 22c acquired at the time instant t. Images Bh of five bright spots appear on the polarized image 12p acquired through illumination by the light emitting units 122h. A thick cross in FIG. 13A indicates the centroid Ma of a geometric shape (here, an ellipse) connecting the positions of the images Bh of the bright spots BP. FIG. 13B is a diagram of the operation state of the illuminating device 120D at the time instant (t+1) in combination with polarized images 32c and 42p acquired at the time instant (t+1). Images By of five bright spots also appear on the polarized image 42p acquired through illumination performed by the light emitting units 122v. A thick cross in FIG. 13B indicates the centroid Mb of a geometric shape (here, an ellipse) connecting the positions of the images By of the bright spots BP.

When five images of the bright spots appear in the parallel nicols image, for example, one ellipse can be determined on the basis of the positions of these five images. When one ellipse can be determined in each of the first and second parallel nicols images, the coordinates of, for example, the centers of these ellipses can be used to translate four polarized images. In other words, the coordinates of, for example, the centers of these ellipses can be used to cancel parallax. As in this example, when five images of the bright spots appear in the parallel nicols image, for example, one ellipse can be determined. Besides the coordinates of the center, for example, information on the parameters such as an inclination angle or the ratio of the major axis to the minor axis (also referred to as ellipticity) is also usable to cancel parallax. An increase in the amount of information enables more precise parallax correction.

Naturally, the number and the arrangement of the light emitting units 122 are not limited to the examples described above. For example, eight light emitting units 122 may be arranged 45° rotated apart from each other to form a circle. In this case, light emitting units that emit first linearly polarized light beams and light emitting units that emit second linearly polarized light beams may be alternately arranged along the circumference. In the structure that includes three or more light emitting units that emit first linearly polarized light beams and three or more light emitting units that emit second linearly polarized light beams, a geometric shape connecting the positions of the centers of the light emitting units that emit first linearly polarized light beams and a geometric shape connecting the positions of the centers of the light emitting units that emit second linearly polarized light beams do not have to be regular polygons. The structure will suffice if the centroid of a geometric shape connecting the positions of the light emitting units that emit first linearly polarized light beams coincides with the centroid of a geometric shape connecting the positions of the light emitting units that emit second linearly polarized light beams. The structure that includes two light emitting units that emit first linearly polarized light beams and two light emitting units that emit second linearly polarized light beams will suffice if the intermediate point between the light emitting units that emit first linearly polarized light beams coincides with the intermediate point between the light emitting units that emit second linearly polarized light beams.

Modified Example 3

Figure 14:
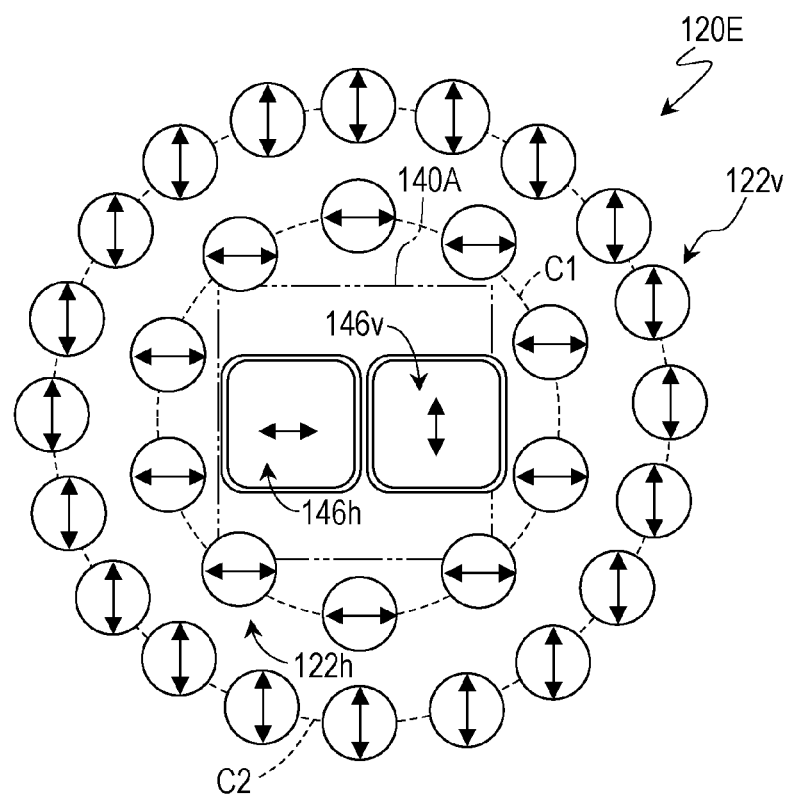
FIG. 14 is a diagram of another example of an arrangement of the multiple light emitting units.

As illustrated in FIG. 14 by way of example, multiple light emitting units 122h and 122v may be concentrically arranged. In an illuminating device 120E illustrated in FIG. 14, multiple light emitting units 122h are densely arranged adjacent to each other on the circumference of a circle C1 and multiple light emitting units 122v are densely arranged adjacent to each other on the circumference of a circle C2, having a larger radius than the circle C1. In this example, the light emitting units 122h are arranged at the positions 36° rotated apart from each other on the circumference of the circle C1, whereas the light emitting units 122v are arranged at the positions 18° rotated apart from each other on the circumference of the circle C2. The multiple light emitting units 122h are located on the same plane and multiple light emitting units 122v are located on the same plane. Typically, the plane on which the multiple light emitting units 122h are arranged is parallel to the plane on which the multiple light emitting units 122v are arranged. The illumination control circuit 162 may control the illuminating device 120E in the same manner as in the example described thus far.

Figure 15A:
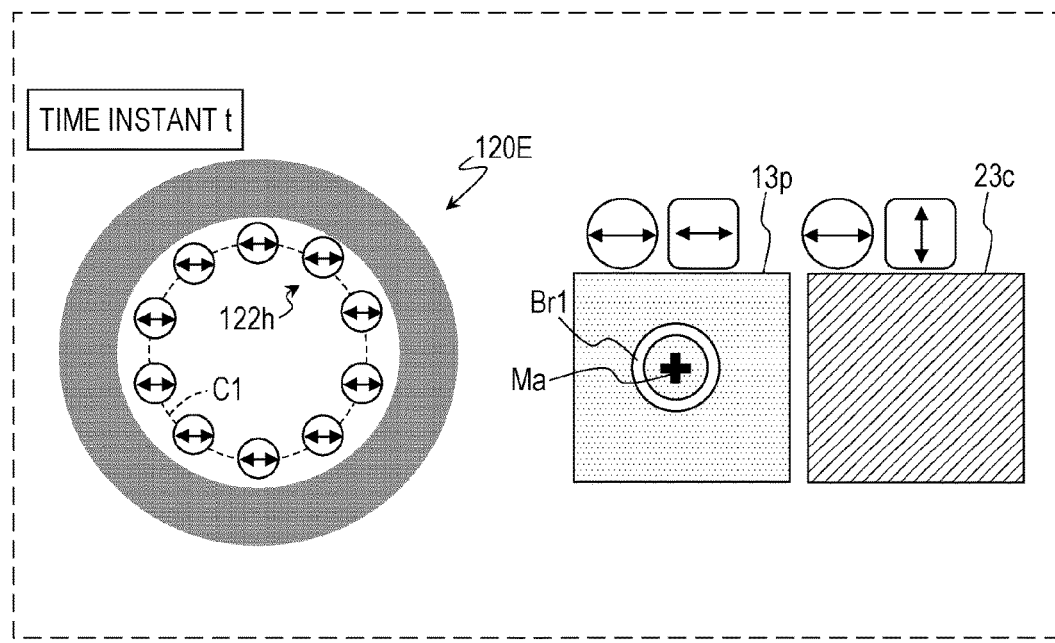
FIG. 15A is a diagram of the operation state of the illuminating device at a certain time instant in combination with polarized images acquired at the time instant.
Figure 15B:
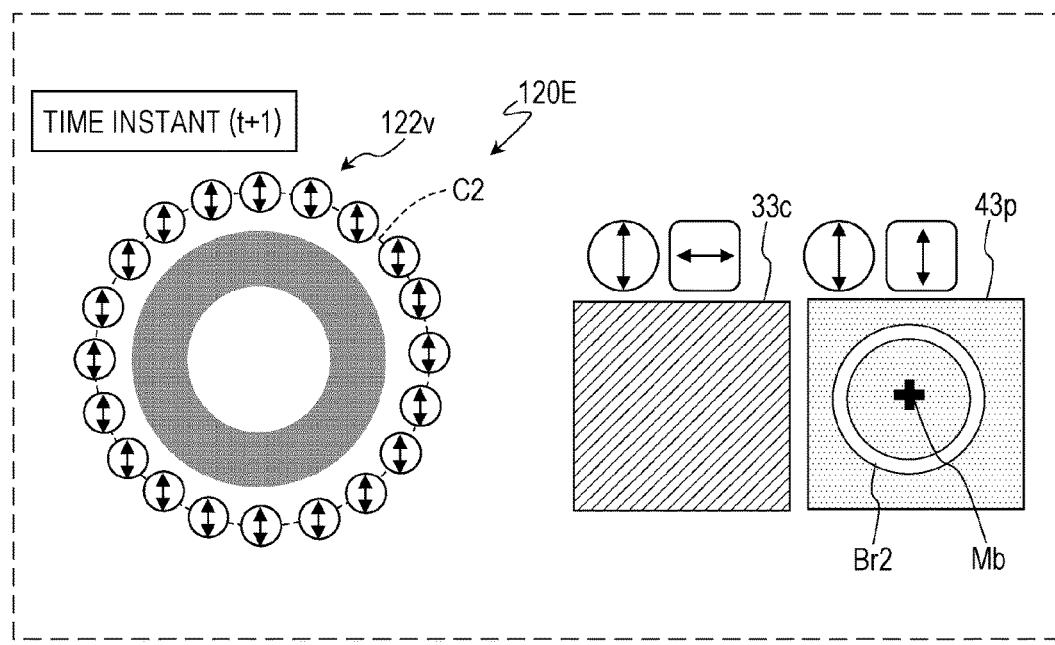
FIG. 15B is a diagram of the operation state of the illuminating device at a subsequent time instant in combination with polarized images acquired at the subsequent time instant.

FIG. 15A is a diagram of the operation state of the illuminating device 120E at a time instant t in combination with polarized images 13p and 23c acquired at the time instant t. A ring-shaped image Br1 brighter than the surroundings appears on the polarized image 13p acquired through illumination performed by the light emitting units 122h. A thick cross in FIG. 15A indicates the centroid Ma of a geometric shape (here, a circle or ellipse) defined by the image Br1. FIG. 15B is a diagram of the operation state of the illuminating device 120E at a time instant (t+1) in combination with polarized images 33c and 43p acquired at the time instant (t+1). A ring-shaped image Br2 brighter than the surroundings appears on the polarized image 43p acquired through illumination performed by the light emitting units 122v. A thick cross in FIG. 15B indicates the centroid Mb of a geometric shape (here, a circle or ellipse) defined by the image Br2.

The structure including densely arranged light emitting units can translate four polarized images using the coordinates of, for example, the centroid of a geometric shape defined by a continuous bright area to cancel parallax. As in this example, when a geometric shape defined by the images reflecting the arrangement of the light emitting units lit during image capturing is a circle or ellipse, the parallax can be cancelled using, for example, the coordinates of the center of the circle or ellipse. Alternatively, information such as the inclination angle or bulge angle of an ellipse may be used to cancel parallax. As in the case of Modification Example 2, described above, an increase in the amount of information enables more precise parallax correction.

Naturally, either the circle C1, defined by the arrangement of the multiple light emitting units 122h, or the circle C2, defined by the arrangement of the multiple light emitting units 122v, may be arranged on the outer side of the other circle. When ine circle can be defined by the arrangement of the multiple light emitting units 122h, another circle can be defined by the arrangement of the multiple light emitting units 122v, and these circles have the same center, the above-described various types of image processing can be performed thereon. The structure illustrated in FIG. 14 by way of example will suffice if the center of the circle C1 connecting the positions of the multiple light emitting units 122h coincides with the center of the circle C2 connecting the positions of the multiple light emitting units 122v.

Modification Example 4

The device disclosed in the present disclosure can be modified into various other imaging devices. FIG. 16 is a diagram of an example of an imaging device having a different structure used together with the illuminating device 120A. An image forming device 100F illustrated in FIG. 16 differs from the image forming device 100A described with reference to FIG. 1 in that the image forming device 100F illustrated in FIG. 16 includes an imaging device 140F instead of the imaging device 140A. Here, the imaging device 140F is combined with the illuminating device 120A. However, instead of the illuminating device 120A, any of the above-described illuminating devices 120B to 120E is naturally usable.

The imaging device 140F includes an objective lens 148s between the image sensor device 142 and a pair of the aperture APh, in which the analyzer 146h is disposed, and the aperture APv, in which the analyzer 146v is disposed. The imaging device 140F also includes a microlens array 144 interposed between the objective lens 148s and the image sensor device 142. The microlens array 144 includes multiple microlenses that face corresponding image-capturing cells of the image sensor device 142.

In this example, light beams that have passed through the analyzer 146h and light beams that have passed through the analyzer 146v pass through the objective lens 148s. Here, the microlens array 144 is disposed in front of the imaging surface of the image sensor device 142. Thus, the light beams that have passed through the analyzer 146h and the light beams that have passed through the analyzer 146v arrive at different areas of the imaging surface. For example, the optical system of the imaging device 140F can be designed so that the light beams that have passed through the analyzer 146h and the light beams that have passed through the analyzer 146v alternately form images on different image-capturing cells. In this case, light beams returned from the subject 200 arrive at different areas on the imaging surface in accordance with the oscillation direction of the electric field vector. The imaging device 140F outputs image signals of two interleaved polarized images having parallax between each other.

The output signals are each separated into signals of two polarized images in a subsequent image process. Thus, two polarized images (typically, parallel nicols images and crossed nicols images) having parallax between each other corresponding to the directions of the transmission axes of the analyzers 146h and 146v can be obtained. Illumination light beams emitted from the illuminating device 120A are switched between first and second linearly polarized light beams so that image capturing is performed through illumination with the respective illumination light beams. As in the case of the image forming device 100A described with reference to FIG. 1, four polarized images can be acquired. Subsequent operations including parallax cancelling may be the same as in the case of the image forming device 100A. The objective lens 148s may be disposed either at the front or back of the analyzers 146h and 146v.

Second Embodiment

Figure 17:
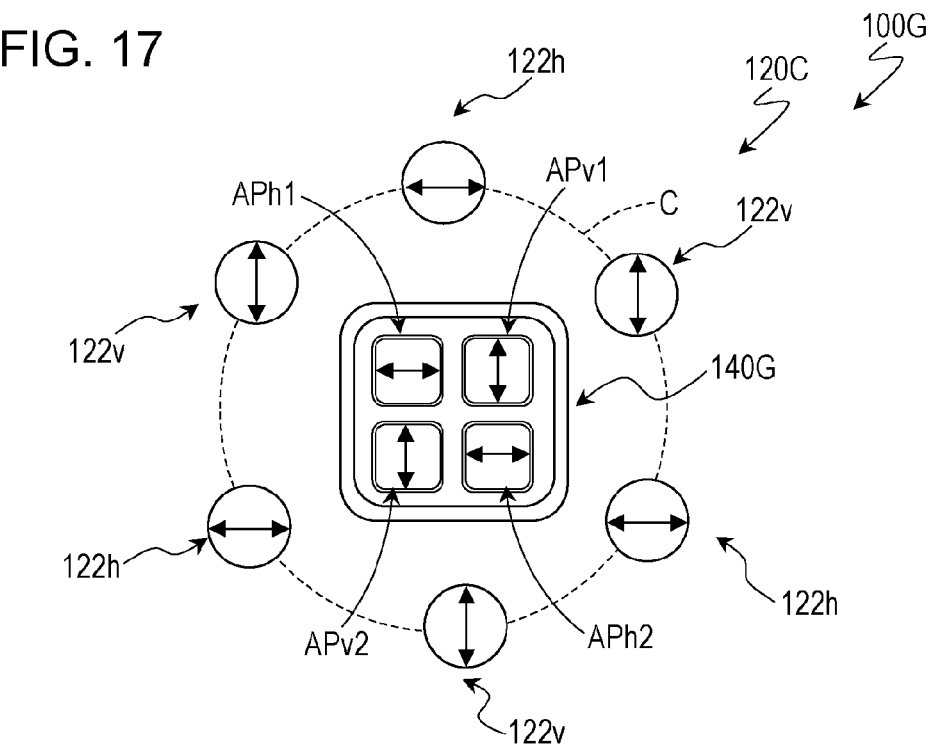
FIG. 17 is a diagram illustrating, by way of example, a structure of an image forming device according to a second embodiment of the present disclosure.

FIG. 17 is a diagram illustrating, by way of example, a structure of an image forming device according to a second embodiment of the present disclosure. FIG. 17 schematically illustrates an illuminating device and an imaging device included in an image forming device 100G according to the second embodiment, viewed from the subject 200. The image forming device 100G includes the illuminating device 120C, described with reference to FIG. 10, and an imaging device 140G. Instead of the illuminating device 120C, any of the above-described illuminating devices 120A, 120B, 120D, and 120E may be used. FIG. 17 does not include an illustration of the control circuit 160.

The imaging device 140G includes four apertures APh1, APh2, APv1, and APv2. In this example, the apertures APh1, APh2, APv1, and APv2 are arranged in a matrix of two rows and two columns. The apertures APh1, APh2, APv1, and APv2 are typically arranged so that the center distance between any two apertures adjacent in the row and column directions in the matrix is uniform.

In this example, the four apertures APh1, APh2, APv1, and APv2 are located on the same plane. The light emitting units 122h and 122v are also located on the same plane. Typically, the plane on which the four apertures APh1, APh2, APv1, and APv2 are located is parallel to the plane on which the light emitting units 122h and 122v are located.

Figure 18:
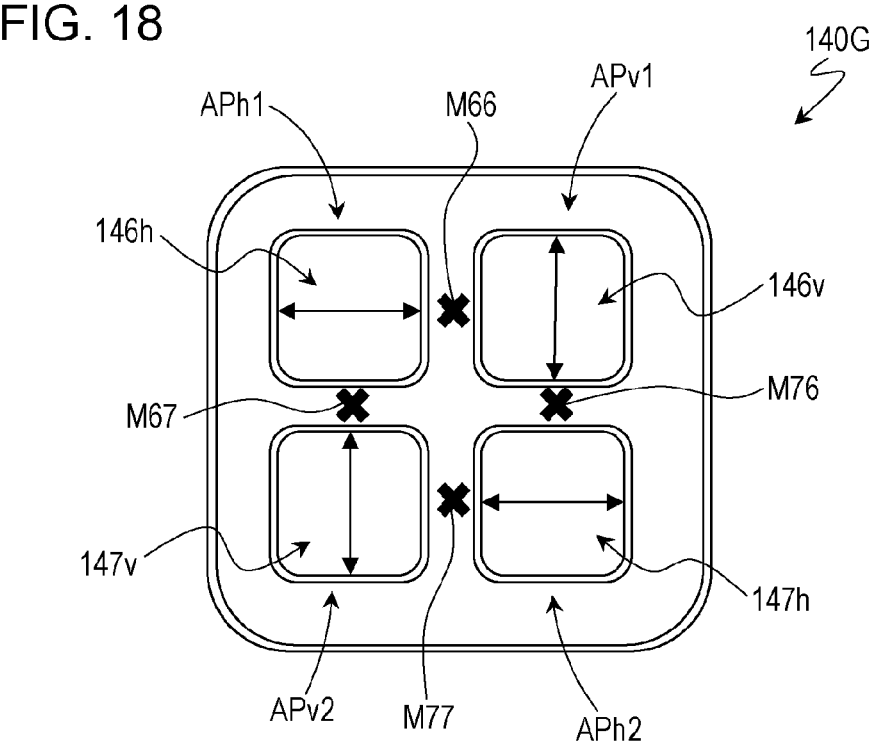
FIG. 18 is a diagram illustrating the relationship between four apertures of an imaging device and the directions of transmission axes of analyzers arranged in the respective apertures.

FIG. 18 is a diagram illustrating the relationship between four apertures of the imaging device 140G and the directions of the transmission axes of analyzers arranged in the respective apertures. The cross marks in FIG. 18 indicate the intermediate points of the line segments each connecting the centers of two apertures adjacent in the row and column directions in the matrix.

Analyzers are disposed in the apertures APh1, APh2, APv1, and APv2. Analyzers disposed in the apertures APv1 and APv2 have transmission axes oriented in the direction different from the direction in which the transmission axes of the analyzers disposed in the apertures APh1 and APh2 are oriented. In the example illustrated in FIG. 18, analyzers 146h and 147h having transmission axes oriented in the direction parallel to the first direction (here, lateral direction in the drawing) are disposed in the apertures APh1 and APh2. The analyzers 146v and 147v having transmission axes oriented in the direction parallel to the second direction (here, vertical direction in the drawing) are disposed in the apertures APv1 and APv2. The analyzers are typically disposed in the four apertures so that the analyzers (here, analyzers 146h and 146v) in the two apertures adjacent to each other in the row and column directions in the matrix have their transmission axes oriented in different directions.

Light beams that have passed through the analyzer 146h, light beams that have passed through the analyzer 147h, light beams that have passed through the analyzer 146v, and light beams that have passed through the analyzer 147v form images at different positions on the imaging surface. Thus, when the imaging device 140G performs image capturing through illumination with, for example, linearly polarized light beams having the electric field vector that oscillates in the direction parallel to the lateral direction of the drawing, the imaging device 140G can acquire two parallel nicols images captured from different viewpoints and two crossed nicols images captured from different viewpoints at the same time. In correspondence with the imaging device 140G including the four apertures APh1, APh2, APv1, and APv2, the imaging device 140G may include four image sensor devices corresponding to the apertures APh1, APh2, APv1, and APv2.

In the first embodiment, a pair of a parallel nicols image and a crossed nicols image having parallax between each other is acquired while the polarized state of illumination light beams is fixed. On the other hand, in the embodiment described here, multiple pairs of a parallel nicols image and a crossed nicols image having parallax between each other are acquired while the polarized state of illumination light beams is fixed. This structure achieves the following advantages.

First, this structure can achieve the same effects as a multi-lens camera. As described above with reference to FIGS. 5A, 5B, and 6, a averaged subtracted polarized image 70, serving as an image of the subject 200, is generated on the basis of the difference between an average parallel nicols image 50ta and an average crossed nicols image 60ta, generated from the pairs of a parallel nicols image and a crossed nicols images having parallax between each other. The averaged subtracted polarized image 70 can thus be said as basically corresponding to an image viewed from the position of substantially the middle between the apertures APh and Apv. In other words, an image acquired by the structure including one aperture APh and one aperture Apv as an image of the subject 200 is an image captured from a single viewpoint.

Here, the acquired polarized images are translated to cancel parallax between the multiple polarized images. As described with reference to FIG. 5B, in the process of cancelling parallax, each of these polarized images typically has a blank area BK having no image data of the subject 200. In other words, the view field is narrowed.

On the other hand, in the structure illustrated in FIGS. 17 and 18 by way of example, two pairs of apertures, in which analyzers having transmission axes oriented in different directions are disposed, can be arranged in each of the row and column directions in the matrix. This structure can form four averaged polarized subtracted images 70 captured from the viewpoints at the intermediate points M66, M67, M76, and M77, between two of the apertures in which analyzers having transmission axes oriented in different directions are disposed, without increasing the number of times of image capturing compared to the case of the first embodiment. The four averaged polarized subtracted images 70 corresponding to the images of the subject 200 viewed from the different viewpoints are used to, for example, compensate the image data of the blank area BK resulting from the cancelling of parallax and to form an image of the subject 200 with a wider area. This structure can easily perform image capturing of, for example, a small subject, such as the pupil.

Secondly, this structure can use the coordinates of the images of the bright spots themselves. A structure including multiple apertures in which analyzers having transmission axes oriented in the same direction can acquire multiple parallel nicols images based on light beams that have passed through analyzers (analyzers 146h and 147h, or analyzers 146v and 147v) having transmission axes oriented in the same direction. These parallel nicols images have parallax between each other. However, the patterns of the images of the bright spots that appear in these parallel nicols images coincide with each other between these images. Instead of the coordinates of the centroid defined by the arrangement of the images of the bright spots in each parallel nicols image, the coordinates of the images of the bright spots themselves can be used for image processing.

Modification Example 4

Figure 19:
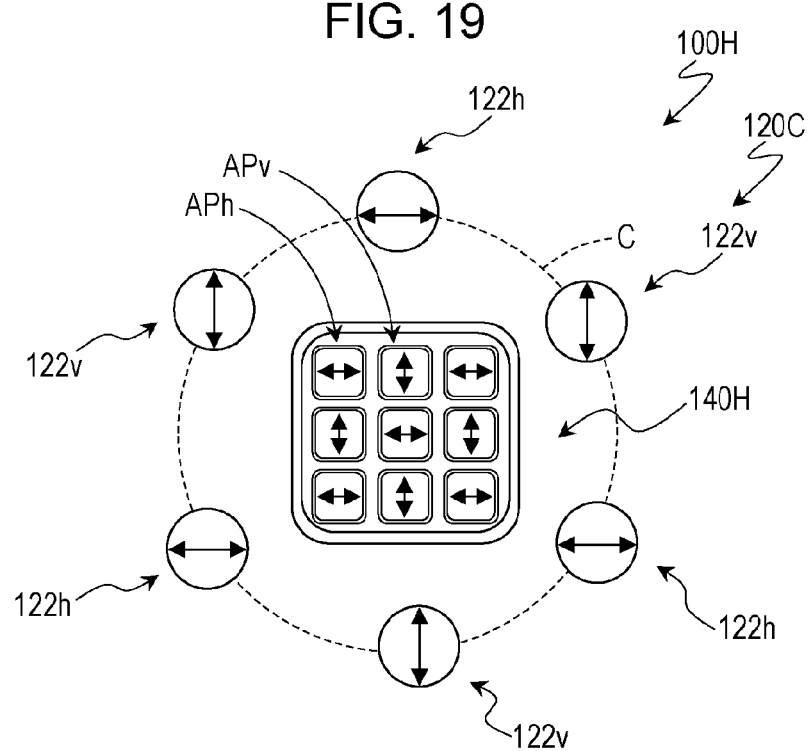
FIG. 19 is a diagram of a modification example of the image forming device according to a second embodiment of the present disclosure.

FIG. 19 is a diagram of a modification example of the image forming device according to the second embodiment of the present disclosure. An imaging device 140H of an image forming device 100H illustrated in FIG. 19 has nine apertures arranged in a matrix. As schematically illustrated in FIG. 19, in this example, five apertures APh and four apertures APv are arranged so that the apertures APh and APv alternate in the row and column directions in the matrix.

Figure 20:
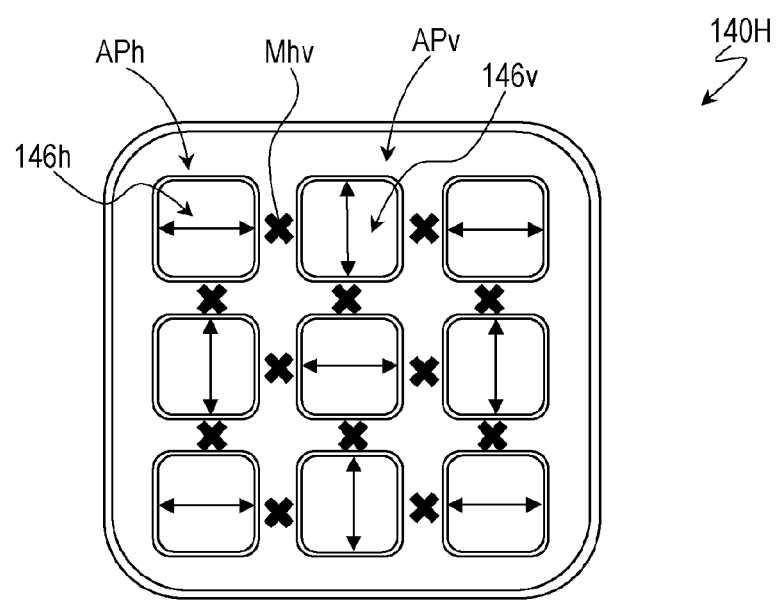
FIG. 20 is an enlarged diagram of an imaging device illustrated in FIG. 19.

FIG. 20 is an enlarged diagram of the imaging device 140H illustrated in FIG. 19. The cross marks in FIG. 19 each indicate the intermediate point of the line segment connecting the centers of two apertures adjacent in the row or column direction in the matrix.

As in the example described with reference to FIGS. 17 and 18, also in this example, the analyzers are arranged so that the analyzers (here, analyzers 146h and 146v) disposed in two apertures adjacent in the row or column direction in the matrix have their transmission axes oriented in different directions. This structure can have, in the row and column directions in the matrix, twelve pairs of apertures in which analyzers having their transmission axes oriented in different directions are arranged. Specifically, this example can form twelve averaged polarized subtracted images 70 each captured from the viewpoint at the intermediate point Mhv between the apertures in which the analyzers having their transmission axes oriented in different directions are disposed, and can, for example, widen the field of view. In this manner, the number of apertures in which analyzers having their transmission axes oriented in different directions may be further increased.

As described above, a typical embodiment of the present disclosure performs image capturing using illumination light beams of various different polarization states to acquire parallel nicols images and crossed nicols images from different viewpoints through the illumination with the illumination light beams. The typical embodiment then cancels parallax between the acquired images on the basis of the positions of the images of the bright spots in two parallel nicols images acquired through illumination with illumination light beams having different polarized states. For example, the typical embodiment can form a averaged polarized subtracted image from two parallel nicols images and two crossed nicols images subjected to parallax cancelling. A averaged polarized subtracted image can be preferably usable to detect a foreign substance adhering to a transparent object and the state of the surface of the transparent object.

An embodiment of the present disclosure can reduce or eliminate the effect of parallax in polarization imaging. An image forming device disclosed herein is usable to detect a foreign substance adhering to a transparent object and the state (for example, projection, depression, or scratch) of the surface of a transparent object. Particularly, the image forming device is preferably usable to observe a subject having a transparent or translucent smooth surface and whose surface state is usually hard to observe through normal image capturing based on the luminance, such as a human or animal eyeball and a transparent pill package. Besides the visual inspection of products or the like, the image forming device of the present disclosure is also applicable to understanding of the state of human or animal (livestock or pet) health or detections of cornea abnormality through visual sensing.

What is claimed is:

1. An image forming device, comprising:
    a plurality of first light emitters that illuminate a subject with first illumination light beams polarized in a first direction;
    a plurality of second light emitters that illuminate the subject with second illumination light beams polarized in a second direction crossing the first direction;
    an imaging device having an imaging surface including a first area, which receives first reflection light beams polarized in the first direction, and a second area, which receives second reflection light beams polarized in the second direction; and
    an image forming circuit that forms an image of the subject on the basis of a first polarized image relating to the first reflection light beams, a second polarized image relating to the second reflection light beams, a third polarized image relating to the first reflection light beams, and a fourth polarized image relating to the second reflection light beams, the first polarized image and the second polarized image being captured by the imaging device while the subject is illuminated with the first illumination light beams, and the third polarized image and the fourth polarized image being captured by the imaging device while the subject is illuminated with the second illumination light beams,
wherein a centroid of a geometric shape connecting positions of the plurality of first light emitters coincides with a centroid of a geometric shape connecting positions of the plurality of second light emitters,
wherein the image forming circuit forms an image of the subject from a translated first polarized image, a translated second polarized image, a translated third polarized image, and a translated fourth polarized image, which are obtained from images of a plurality of first bright spots and images of a plurality of second bright spots, the first bright spots appearing on the first polarized image when the first illumination light beams are mirror-reflected off the subject, and the second bright spots appearing on the fourth polarized image when the second illumination light beams are mirror-reflected off the subject, and
wherein the image forming circuit forms an image of the subject by calculating a difference between a first average image and a second average image, the first average image being obtained by averaging the translated first polarized image and the translated fourth polarized image, the second average image being obtained by averaging the translated second polarized image and the translated third polarized image.

2. The image forming device according to claim 1,
wherein the plurality of first light emitters and the plurality of second light emitters are arranged in a circle, and
wherein a center of a circle that passes the positions of the plurality of first light emitters coincides with a center of a circle that passes the positions of the plurality of second light emitters.

3. The image forming device according to claim 1,
wherein the plurality of first light emitters and the plurality of second light emitters surround the imaging device when viewed from the subject.

4. The image forming device according to claim 1, further comprising an illumination control circuit,
wherein the plurality of first light emitters each include a first light source,
wherein the plurality of second light emitters each include a second light source, and
wherein the illumination control circuit lights the first light source and the second light source at a different time point.

5. The image forming device according to claim 1,
wherein the image forming circuit translates the first polarized image so that a centroid of the images of the plurality of first bright spots in the first polarized image is located at a center of the first polarized image, and translates the third polarized image in a direction the same as a direction in which and by a distance the same as a distance by which the first polarized image is translated, and
wherein the image forming circuit translates the fourth polarized image so that a centroid of the images of the plurality of second bright spots in the fourth polarized image is located at a center of the fourth polarized image, and translates the second polarized image in a direction the same as a direction in which and by a distance the same as a distance by which the fourth polarized image is translated.

6. The image forming device according to claim 1, further comprising:
at least one first image sensor device including the first area; and
at least one second image sensor device including the second area.

7. An image forming apparatus, comprising:
first emitters that illuminate an object with first light polarized in a first direction during a first period;
second emitters that illuminate the object with second light polarized in a second direction different from the first direction during a second period different from the first period;
a first polarizing filter that selectively transmits light polarized in the first direction;
a second polarizing filter that selectively transmits light polarized in the second direction;
an imaging device that includes a first area and a second area, the first area including first pixels and the second area including fourth pixels, the first pixels including second pixels and third pixels, the fourth pixels including fifth pixels and sixth pixels; and
an image forming circuit,
wherein first surfaces, included in the first emitters, and second surfaces, included in the second emitters, are located on a first plane,
wherein the first light is emitted from the first surfaces and the second light is emitted from the second surfaces,
wherein third surfaces, included in the first polarizing filter, and fourth surfaces, included in the second polarizing filter, are located on a second plane,
wherein the third surfaces receive light from outside of the first polarizing filter and the fourth surfaces receive light from outside of the second polarizing filter,
wherein a geometric barycenter of points located at the centers of the first surfaces and a geometric barycenter of points located at the centers of the second surfaces are located at an identical point,
wherein the object reflects the first light and outputs first resulting light and second resulting light,
wherein the first polarizing filter receives the first resulting light and outputs first polarized light that is polarized in the first direction,
wherein the second polarizing filter receives the second resulting light and outputs second polarized light that is polarized in the second direction,
wherein the imaging device receives the first polarized light at the first pixels and outputs a first image including first pixel values at the first pixels, the first pixel values including second pixel values at the second pixels and third pixel values at the third pixels, the second pixel values being greater than the third pixel values,
wherein the imaging device receives the second polarized light at the fourth pixels and outputs a second image including fourth pixel values at the fourth pixels,
wherein the object reflects the second light and outputs third resulting light and fourth resulting light,
wherein the first polarizing filter receives the third resulting light and outputs a third polarized light that is polarized in the first direction, wherein the second polarizing filter receives the fourth resulting light and outputs a fourth polarized light that is polarized in the second direction, wherein the imaging device receives the third polarized light at the first pixels and outputs a third image including fifth pixel values at the first pixels, wherein the imaging device receives the fourth polarized light at the second pixels and outputs a fourth image including sixth pixel values at the fourth pixels, the sixth pixel values including seventh pixel values at the fifth pixels and eight pixel values at the sixth pixels, the seventh pixel values being greater than the eighth pixel values, wherein the first area and the second area are expressed by using an x-y coordinate system, wherein the image forming circuit calculates a first coordinate value (Xa, Ya) indicating a geometric barycenter of coordinate values of the second pixels and a second coordinate value (Xb, Yb) indicating a geometric barycenter of coordinate values of the fifth pixels, wherein when a pixel value, included in the first image, at a pixel included in the first pixels and located at a coordinate value (x, y) is I1, the image forming circuit calculates x'=(x−Xa−p) and y'=(y−Ya−q) and determines a pixel value at a coordinate value (x', y') as I1, wherein when a pixel value, included in the second image, at a pixel included in the fourth pixels and located at a coordinate value (x, y) is I2, the image forming circuit calculates x'=(x−Xb−p) and y'=(y−Yb−q) and determines a pixel value at a coordinate value (x', y') as I2, wherein when a pixel value, included in the third image, at a pixel included in the first pixels and located at a coordinate value (x, y) is I3, the image forming circuit calculates x'=(x−Xa−p) and y'=(y−Ya−q) and determines a pixel value at a coordinate value (x', y') as I3, wherein when a pixel value, included in the fourth image, at a pixel included in the fourth pixels and located at a coordinate value (x, y) is I4, the image forming circuit calculates x'=(x−Xb−p) and y'=(y−Yb−q) and determines a pixel value at a coordinate value (x', y') as I4, wherein p and q are real numbers, wherein the image forming circuit calculates a pixel value Ii at a coordinate value (xi, yi) using an equation that is Ii={I1(x'=xi, y'=yi)+I4(x'=xi, y'=yi)}/2−{I2(x'=xi, y'=yi)+I3(x'=xi, y'=yi)}/2, and wherein i is a natural number.

* * * * *